US009356170B2

(12) United States Patent
Brown et al.

(10) Patent No.: US 9,356,170 B2
(45) Date of Patent: May 31, 2016

(54) THZ DISTRIBUTED DETECTORS AND ARRAYS

(71) Applicants: Elliott R. Brown, Beavercreek, OH (US); John R. Middendorf, Medway, OH (US); John S. Cetnar, West Manchester, OH (US)

(72) Inventors: Elliott R. Brown, Beavercreek, OH (US); John R. Middendorf, Medway, OH (US); John S. Cetnar, West Manchester, OH (US)

(73) Assignee: WRIGHT STATE UNIVERSITY, Dayton, OH (US)

( * ) Notice: Subject to any disclaimer, the term of this patent is extended or adjusted under 35 U.S.C. 154(b) by 206 days.

(21) Appl. No.: 14/215,804

(22) Filed: Mar. 17, 2014

(65) Prior Publication Data
US 2015/0280036 A1    Oct. 1, 2015

Related U.S. Application Data

(60) Provisional application No. 61/790,433, filed on Mar. 15, 2013, provisional application No. 61/811,510, filed on Apr. 12, 2013.

(51) Int. Cl.
*H01L 31/0352* (2006.01)
*H01L 31/108* (2006.01)
*G01N 21/552* (2014.01)

(52) U.S. Cl.
CPC ...... *H01L 31/035281* (2013.01); *G01N 21/554* (2013.01); *H01L 31/035209* (2013.01); *H01L 31/108* (2013.01)

(58) Field of Classification Search
CPC ............... H01L 31/035281; H01L 31/035209; H01L 31/108
See application file for complete search history.

(56) References Cited

U.S. PATENT DOCUMENTS

| 7,501,636 | B1* | 3/2009 | Son | G01J 5/02 250/370.14 |
|---|---|---|---|---|
| 2005/0156182 | A1* | 7/2005 | Hehemann | H01L 27/1463 257/82 |
| 2006/0289761 | A1* | 12/2006 | Nabet | H01L 31/108 250/336.1 |
| 2007/0194357 | A1* | 8/2007 | Oohashi | H01L 31/108 257/292 |
| 2008/0042563 | A1* | 2/2008 | Niigaki | H01J 40/06 313/542 |
| 2008/0217542 | A1* | 9/2008 | Verma | H01L 31/022408 250/370.01 |
| 2009/0262766 | A1* | 10/2009 | Chen | H03C 7/027 372/26 |

OTHER PUBLICATIONS

Nasipuri et al., Nonparametric distributed detector using Wilcoxon statistics, Mar. 1997, Signal Processing, vol. 57, Iss. 2, pp. 139-146.*

(Continued)

*Primary Examiner* — David Porta
*Assistant Examiner* — Jeremy S Valentiner
(74) *Attorney, Agent, or Firm* — Kegler Brown Hill & Ritter Co., L.P.A.; James Pingor

(57) ABSTRACT

Terahertz (THz) distributed detectors, and arrays of detectors that utilize structured surface plasmonic effects for more efficient coupling to free space are discussed. One example distributed detector includes a detector junction comprising a Schottky or tunneling interface between a semiconductor and a detector metal, an ohmic junction comprising an ohmic interface between the semiconductor and an ohmic metal, and a gap that separates the detector junction from the ohmic junction. Structured surface plasmons concentrate an electric field in the gap when the distributed detector is exposed to THz radiation polarized perpendicular to the gap.

20 Claims, 22 Drawing Sheets

(56) References Cited

OTHER PUBLICATIONS

Manohara et al., Carbon Nanotube Schottky Diodes Using Ti-Schottky and Pt-Ohmic Contacts for High Frequency Applications, May 2005, Nano Letters, vol. 5, No. 7, pp. 1469-1474.*
Yamada et al., Terahertz wire-grid polarizers with micrometer-pitch Al gratings, Feb. 2009, Optics Letters, vol. 34, No. 3, pp. 274-276.*
William L. Barnes, Alain Dereux, & Thomas W. Ebbesen, Surface plasmon subwavelength optics, Nature, Aug. 14, 2003, 824-830, vol. 424, Nature Publishing Group.
T.W. Ebbesen, H.J. Lezec, H.F. Ghaemi, T. Thio & P.A. Wolff, Extraordinary optical transmission through sub-wavelength hole arrays, Naure, Feb. 12, 1989, 667-669, vol. 391, Macmillan Publishers Ltd.
L. Martin-Moreno, F.J. Garcia-Vidal, H.J. Lezec, K.M. Pellerin, T. Thio, J.B. Pendry & T.W. Ebbesen,Theory of Extraordinary Optical Transmission through Subwavelength Hole Arrays, Physical Review Letters, Feb. 5, 2001, 1114-1117, vol. 89, No. 6.
M. Palamaru & S. Astilean, Sub-Wavelength Metallic Gratings of Very High Transmission Efficiency, Journal of Optoelectronics and Advanced Materials, Jun. 1999, 35-40, vol. 1, No. 2.
H.F. Ghaemi, Tineke Thio & D.E. Grupp, Surface plasmons enhance optical transmission through subwavelength holes, Physical Review B, Sep. 15, 1998, 6779-6782, vol. 58, No. 11.
A. Barbara, P. Quemerais, E. Bustarret & T. Lopez-Rios, Optical transmission through subwavelength metallic gratings, Physical Review B, Oct. 8, 2002, 1-4, vol. 66.
John S. Cetnar, John R. Middendorf & Elliott R. Brown, Extraordinary optical transmission and extinction in a Terahertz wire-grid polarizer, Applied Physics Letters, Jun. 8, 2012, 1-3, vol. 100.
Hua Cao & Ajay Nahata, Resonantly enhanced transmission of terahertz radiation through a periodic array of subwavelength apertures, Optics Express, Mar. 22, 2004, vol. 12, No. 6.

Miguel Beruete, Mario Sorolla, I. Campillo, J.S. Dolado, Luis Martin-Moreno, J. Bravo-Abad & F.J. Garcia-Vidal, Enhanced Millimeter Wave Transmission Through Quasioptical Subwavelength Perforated Plates, IEEE Transactions on Antennas and Propagation, Jun. 2005, 1897-1903, vol. 53, No. 6.
C.W. Berry, M.Unlu, M.R. Hashemi & M. Jarrahi, Use of Plasmonic Gratings for Enhancing the Quantum Efficiency of Photoconductive Terahertz Sources, The Journal of Infrared, Millimeter, and Terahertz Waves, Sep. 23-28, 1-2, IEEE.
Stefan A. Maier, Plasmonics: Fundamentals and Applications, 2007, 1-223, Springer Science+Business Media LLC, New York.
J.B. Pendry, L. Martin-Moreno, F.J. Garcia-Vidal, Mimicking Surface Plasmons with Structured Surfaces, Science, Aug. 6, 2004, 847-848, vol. 305.
X.R. Huang, R.W. Peng, Z. Wang, F. Gao & S.S. Jiang, Charge-oscillation-induced light transmission through subwavelength slits and holes, Physical Review A, 2007, 1-4, vol. 76.
Xian-Rong Huang, Ru-Wen Peng & Ren-Hao Fan, Making Metals Transparent for White Light by Spoof Surface Plasmons, Physical Review Letters, Dec. 7, 2010, 1-4, vol. 105.
X.F. Li & S. F. Yu, Long-wavelength optical transmission of extremely narrow slits via hybrid surface-plasmon and Fabry—Pérot modes, Journal of Applied Physics, Jul. 7, 2010, 1-5, vol. 108.
Bradley M. Ratliff, Daniel A. Lemaster, Robert T. Mack, Pierre V. Villeneuve, Jeffrey J. Weinheimer & John R. Middendorf, Detection and tracking of RC model aircraft in LWIR microgrid polarimeter data, SPIE, Sep. 9, 2011, 1-13, vol. 8160.
Itsunari Yamada, Keisuke Takano, Masanori Hangyo, Mitsunori Saito & Wataru Watanabe, Terahertz wire-grid polarizers with micrometer-pitch A1 gratings, Optics Letters, Feb. 1, 2009, 274-276, vol. 34, No. 8.

* cited by examiner

THZ DISTRIBUTED DETECTORS AND ARRAYS

CROSS-REFERENCE TO RELATED APPLICATIONS

This application claims the benefit of U.S. Provisional Patent application Ser. No. 61/790,433 entitled 'SPOOF-SURFACE-PLASMON-COUPLED THz COMPONENTS AND DEVICES' and filed Mar. 15, 2013 and claims the benefit of U.S. Provisional Patent application Ser. No. 61/811,510 entitled 'Structured Surface-Plasmon THz Components and Devices' and filed Apr. 12, 2013. The entireties of the above-noted applications are incorporated by reference herein.

BACKGROUND

THz radiation has many potential applications ranging from medical imaging, security, and chemical sensing, to communications, radar, and manufacture monitoring, etc. However, conventional THz detection technology has experienced limited advancement in the field, precluding the realization of several of these applications for performance or affordability reasons.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a distributed detector. One such example includes a detector junction comprising a Schottky interface between a semiconductor and a detector metal, an ohmic junction comprising an ohmic interface between the semiconductor and an ohmic metal, and a gap in the metal that separates the detector junction from the ohmic junction. Structured surface plasmons concentrate an electric field in the gap when the distributed detector is exposed to THz radiation of the correct polarization perpendicular to the gap.

In another aspect, the subject innovation comprises a polarimetric distributed detector. One example includes a plurality of unit cells. Each unit cell of the plurality of unit cells can be aligned to detect a distinct linear polarization. Each unit cell includes a Schottky or tunnel junction, an ohmic contact, and a gap between the Schottky or tunnel junction and the ohmic contact. Structured surface plasmons concentrate an electric field in the gap when the unit cell is exposed to THz radiation.

In further aspects, embodiments of the subject innovation can include a shared-gap distributed detector. One such example includes a first detector metal surrounded by a first detector junction, a second detector metal surrounded by a second detector junction, a first ohmic metal surrounded by a first ohmic contact, and a second ohmic metal surrounded by a second ohmic contact. This distributed detector can also include a gap that separates the first detector junction from the first ohmic contact and from the second ohmic contact, and separates the second detector junction from the first ohmic contact and from the second ohmic contact. Structured surface plasmons concentrate an electric field in the gap when the shared-gap distributed detector is exposed to THz radiation polarized perpendicular to the gap.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
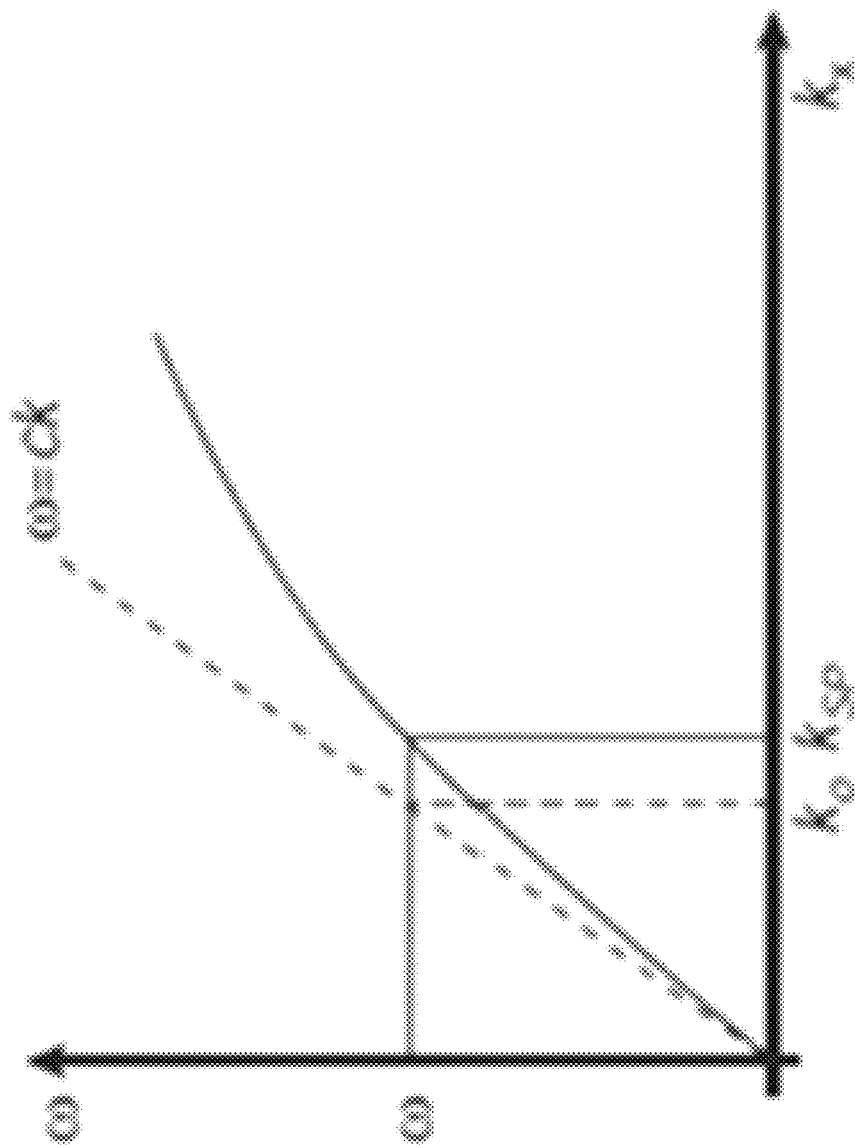
FIG. 1 illustrates the surface plasmon dispersion curve on a metallic surface.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

Extraordinary Optical Transmission (EOT) is defined as the greatly enhanced transmission of light through sub-wavelength apertures compared to what is expected by geometrical optics. This occurs, of course, without any amplification of the net output power with respect to the net input power. EOT occurs in an opaque metallic film on which the apertures have been patterned in a repeating periodic grid or array. The array may be 2D-periodic, as in the case of periodically patterned holes, or 1D-periodic, as in the case of a wire grid. Many examples of these structures and their behavior exist, most of which focus on EOT in the visible or infrared regions of the electromagnetic (EM) spectrum. The physical mechanism explaining EOT is usually the resonant coupling of electromagnetic radiation in the air with surface plasmons (SPs) on the conductor. EOT can also be seen in longer wavelength (lower frequency) regions of the electromagnetic spectrum, from microwave through the THz regions. However, in these regions, the mechanism for EOT is not SP coupling, strictly speaking. In metals, the high concentration of free electrons ensures that well-confined SPs can exist only for frequencies relatively close to the conductor's plasma frequency $\omega_p$. For most metals, $\omega_p$ is in the ultraviolet. Thus, SPs are supported in the visible and near-infrared regions but are very weak in the THz region.

Referring initially to the drawings, FIG. 1 illustrates the surface plasmon dispersion curve on a metallic surface, showing the surface plasmon wavevector $k_{SP}$ and the EM radiation wavevector $k_0$. As can be seen, the SP wavevector, $k_{SP}$, is larger than the EM wavevector, $k_0$ (i.e., the light line) for any given frequency. This means that the SPs have more momentum than light at any given frequency. Because of this momentum difference, the coupling of light with SPs cannot occur without a momentum change. Photons of the incident radiation are required to gain momentum in order to excite SPs on the metallic surface. Likewise, SPs already propagating along the metallic surface cannot radiate away as light without losing momentum. Therefore, a SP wave is said to be confined to the conductor's surface. As the SPs are confined to the surface, their EM fields perpendicular to the surface decay with distance (in both the metal and air directions). The amount of the confinement increases with increasing $k_{sp}$ and decreases significantly for $\omega<<\omega_p$, where $k_{SP}$ asymptotically approaches $k_0$. In the THz region, the SP wave vector $k_{SP}$ is approximately equal to $k_0$ ($k_{SP} \approx k_0$), due to the large negative real part of the complex permittivity ($|\epsilon| \approx 10^5$) characteristic of metal conductors in the THz region. This, in turn, causes the SPs to be delocalized, hence, SPs at THz frequencies are not strongly confined to the conductor's surface and easily radiate away.

However, at THz and lower frequencies SP-like behavior can be caused by a different mechanism. In an array of periodically spaced sub-wavelength apertures on a thin metal film, the incident radiation causes surface currents to flow into and around the apertures. These currents create oscillating electric and magnetic dipoles across the apertures. These dipoles act like surface plasmons, and are referred to as "spoof" or "structured" surface plasmons (SSPs). This is essentially the same mechanism that produces the interesting electromagnetic effects seen in metamaterials at THz and lower frequencies, and can be observed in 2D-periodic arrays of circular holes, for example.

SSPs can also be observed in 1D-periodic arrays of narrow gaps such as those that occur in a metal-wire grid on an insulating substrate. This is justified physically by the surface currents and the electric and magnetic dipoles discussed above, whereby the gaps (e.g., the area exposed to the substrate between the metal strips of the wire grid, etc.) can act as sub-wavelength radiating dipoles. A wire grid of periodically spaced apertures in a metal film can support SSPs when $d<a<<\lambda$ (d=aperture width, a=grid period, and $\lambda$=free-space radiation wavelength).

Given the excitation of structured surface plasmons in an array of apertures, there is the possibility of strong concentration of electromagnetic energy. Given efficient re-radiation of this energy by the induced dipoles, there can also be high transmission through the array to the opposite side. The degrees of concentration and transmission enhancement created can indeed be "extraordinary," meaning that they are both significantly larger than expected from the principles of geometrical optics. Electric field enhancements as high as $10^8$ can be seen in 1D-periodic arrays. Further, the enhancement increases with increasing fill factor in 1D arrays (fill factor, FF=w/(w+d) where w is conductor width and d is aperture width). In a periodic arrangement with w+d<$\lambda$, the apertures collectively act as an antenna array with constructive interference in the direction perpendicular to the substrate, and the transmission of power from input to output can approach unity.

Figure 2:
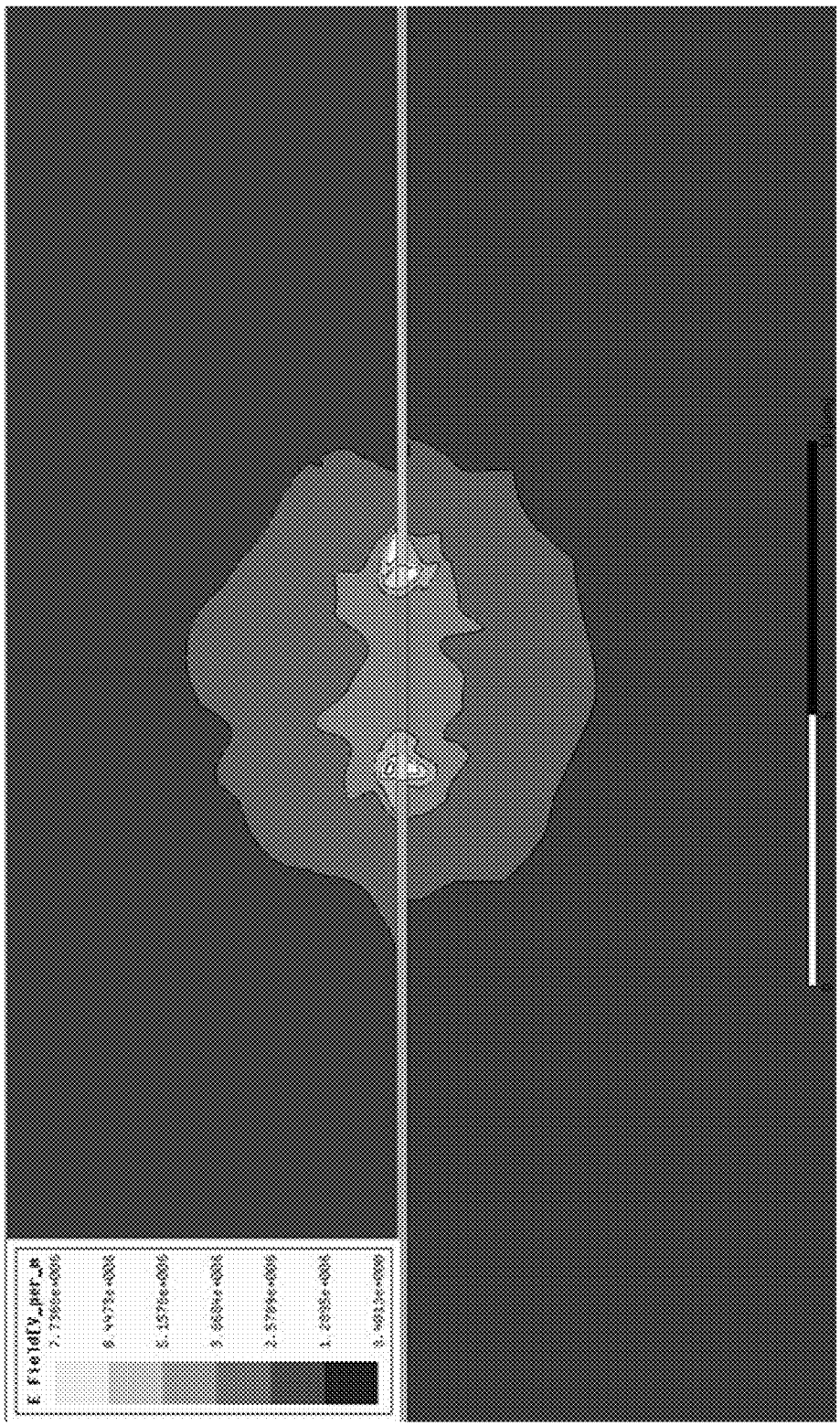
FIG. 2 illustrates a structured surface plasmon concentration effect producing very high electric field intensity in the context of a THz wire-grid polarizer.

More germane to various embodiments of the subject innovation, the concentration effect can produce very high electric field intensities across the apertures. FIG. 2 illustrates this effect in the context of the THz wire-grid polarizer: a side view of the electric field magnitude in the gap region for a 95% fill factor at 530 GHz. The field is concentrated inside the gap, where the gap is the area exposed to the substrate between the metal strips. The slight asymmetry in the electric field strength with respect to the gap bisector is associated with asymmetric meshing in the FEM algorithm used in the calculation. The wire grid consists of 40 micron periodic aluminum strips (1D array) mounted on a polycarbonate substrate (conductor width=32 micron, gap width=8 micron, incident EM radiation at 530 GHz). The full-wave electromagnetic simulations were carried out on a unit cell yielding the electric-field map of FIG. 2.

Figure 3:
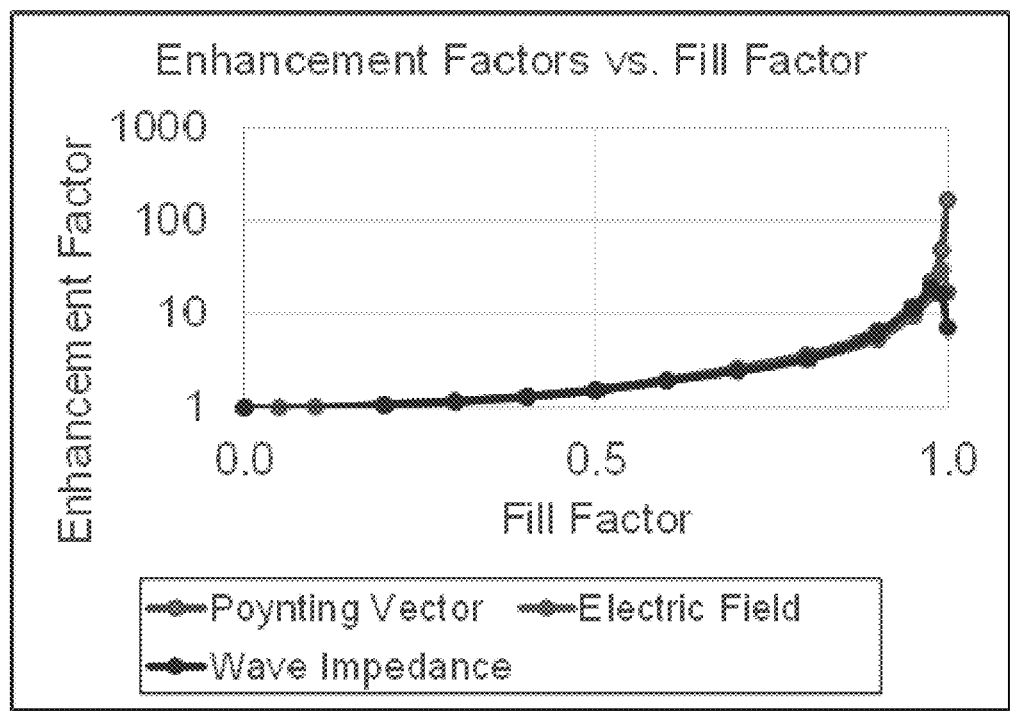
FIG. 3 illustrates the results of full-wave simulations repeated for many different gap sizes at a fixed period, graphing enhancement versus fill factor at 530 GHz.
Figure 3:
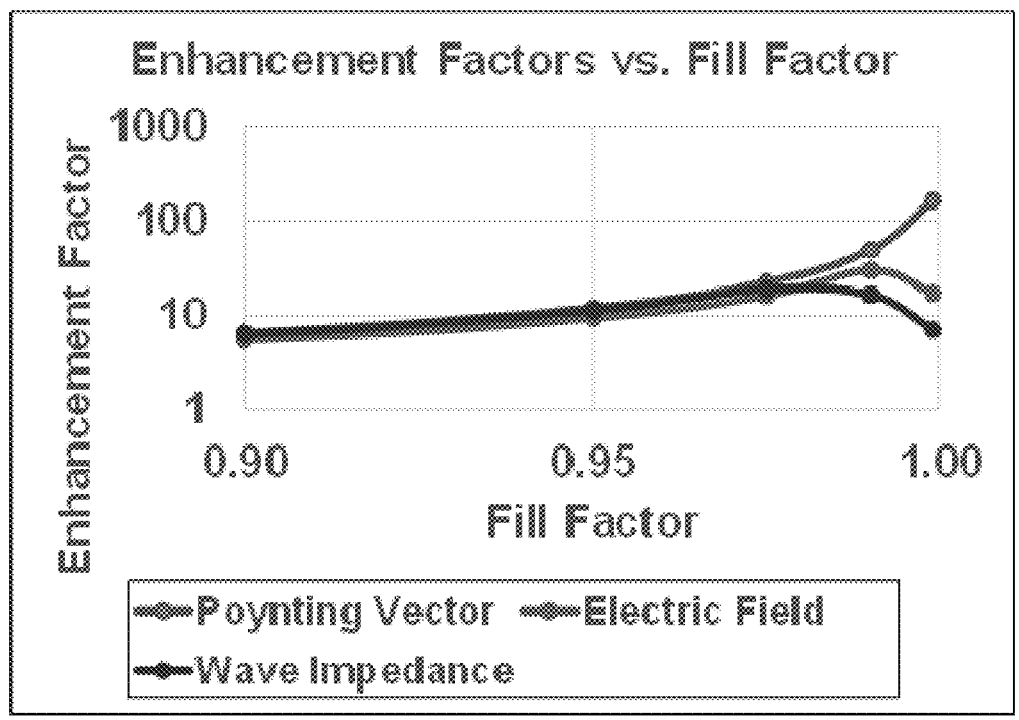

The enhancement effects can be clearly seen in FIG. 3, summarizing the results of the full-wave simulations repeated for many different gap sizes at a fixed period, graphing enhancement versus fill factor at 530 GHz at 310, with the fill factor range of 0.90 to 1.00 blown up in 320, where a maximum is achieved. The electric field energy enhancement factor is more than 160, the electric field magnitude enhancement factor is more than 24, and the wave impedance enhancement factor is more than 13 compared to the incident free-space field.

Figure 4:
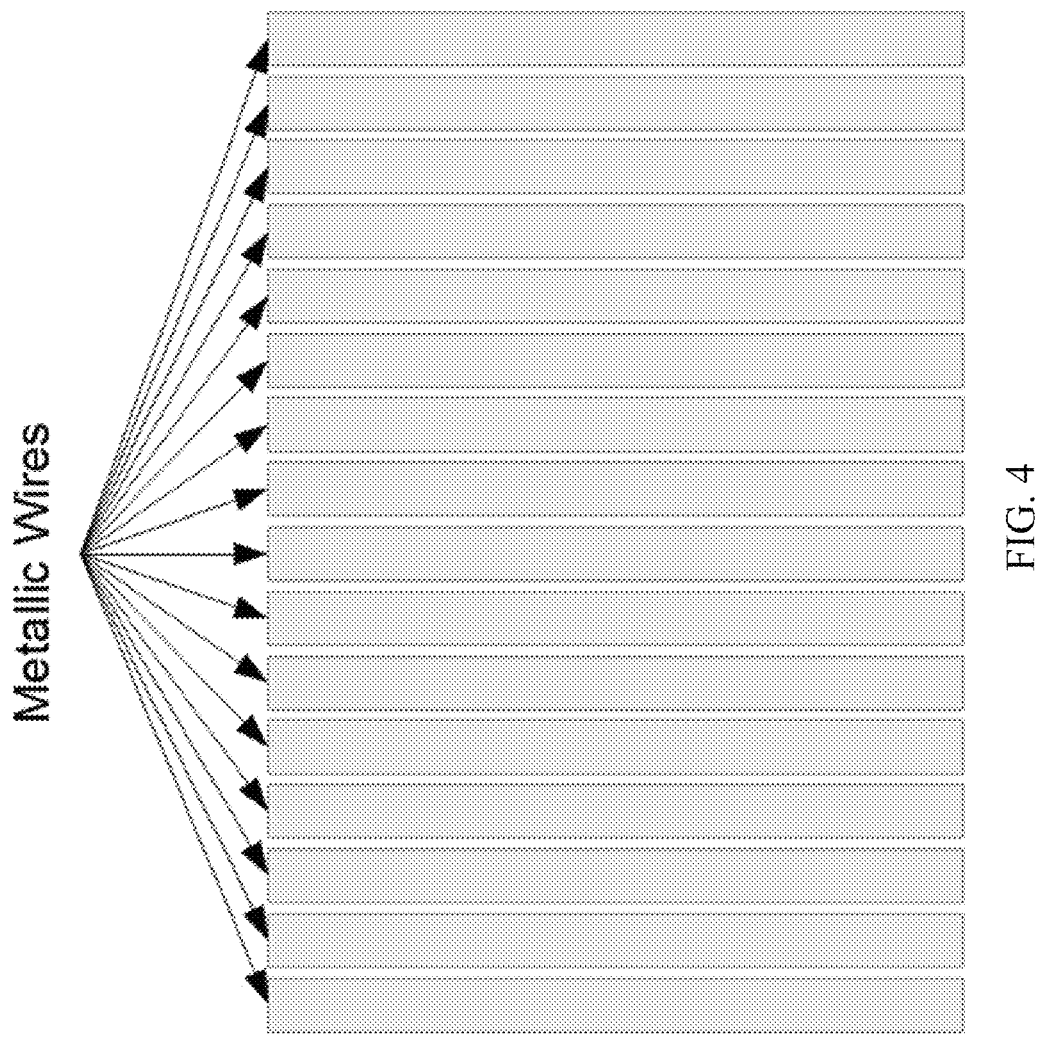
FIG. 4 illustrates an overhead view of a wire-grid polarizer.

The wire- or strip-grid polarizer is a simple device that is composed of many parallel "wires" on a dielectric substrate. The wires are metallic and have no contact with each other. The thickness can vary, and is usually similar to the width; however, this is not a requirement, and the dimensions can vary greatly. The width or diameter is therefore determined by fill factor and period specifications. FIG. 4 illustrates an overhead view of such a polarizer, corresponding to the cross-sectional view of FIG. 2. The length of the wires or strips and the number of them present can be determined by the desired size of the polarizer: a wider polarizer will have more parallel wires, and a taller polarizer will have longer wires.

Wire-grid and strip-grid polarizers are components that can be used to modify an electromagnetic signal. This includes, but is not limited to, modulating signal strength in linearly polarized signals, converting from circularly polarized signals to linearly polarized signals, and splitting signals into two separate signals with differing propagation directions. The polarizers can be engineered to use structured-surface-plasmonic effects to increase electric field attenuation when the polarization is parallel to the wires or strips, which also increases the amount of signal reflected off of the polarizer in another direction. The same wire and strip grid polarizers exhibit little attenuation when the electric field points in a perpendicular direction to the wires. This effectively increases the metric known as "extinction ratio," which is a measure of signal transmission in the perpendicular (S) orientation divided by transmission in the parallel (P) orientation, shown in Eq. 1:

$$\text{Extinction} = \frac{Signals_S}{Signals_P} \quad (1)$$

Figure 5:
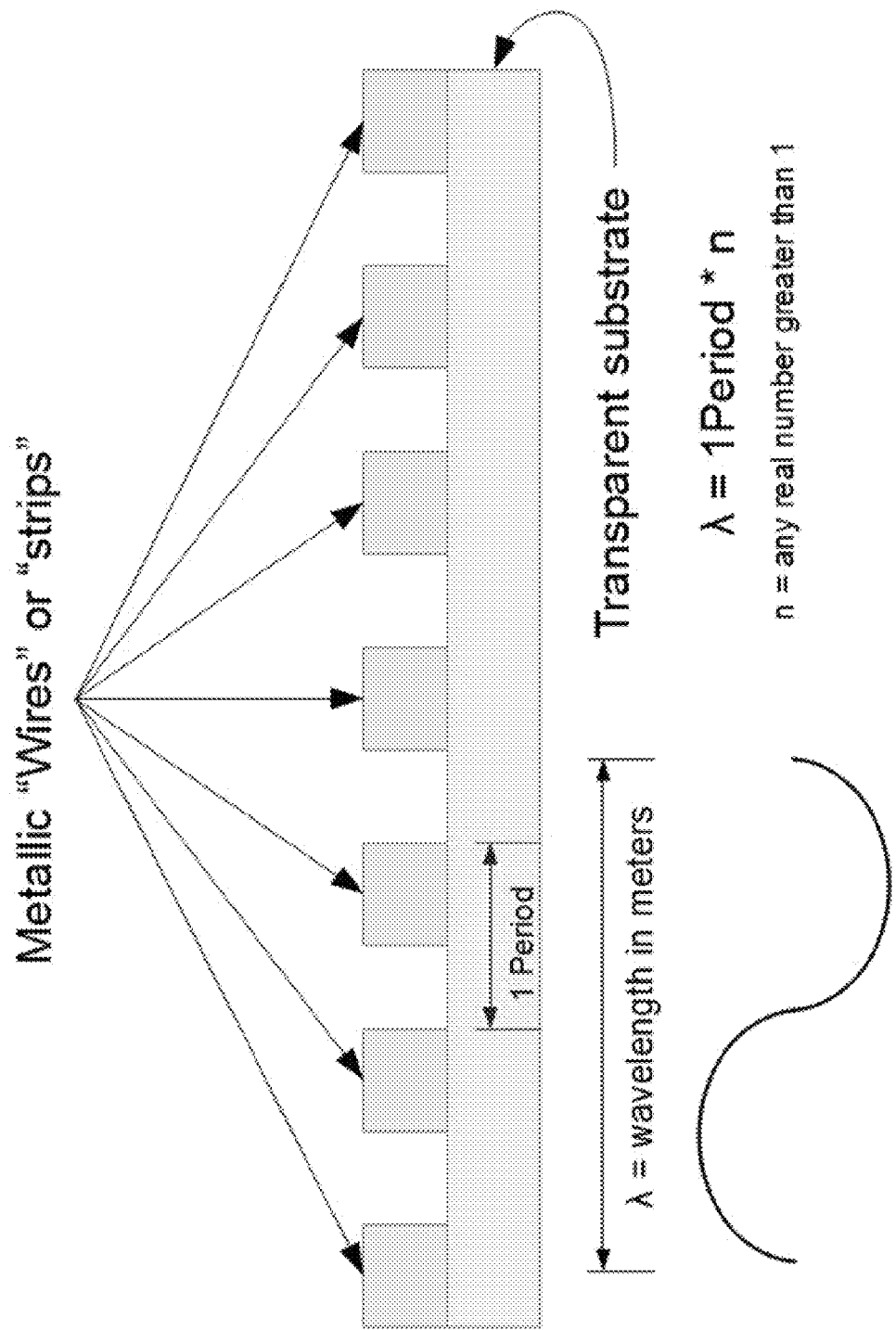
FIG. 5 illustrates a first structured-surface-plasmonic engineering technique, decreasing the polarizer period to sub-wavelength dimensions.
Figure 6:
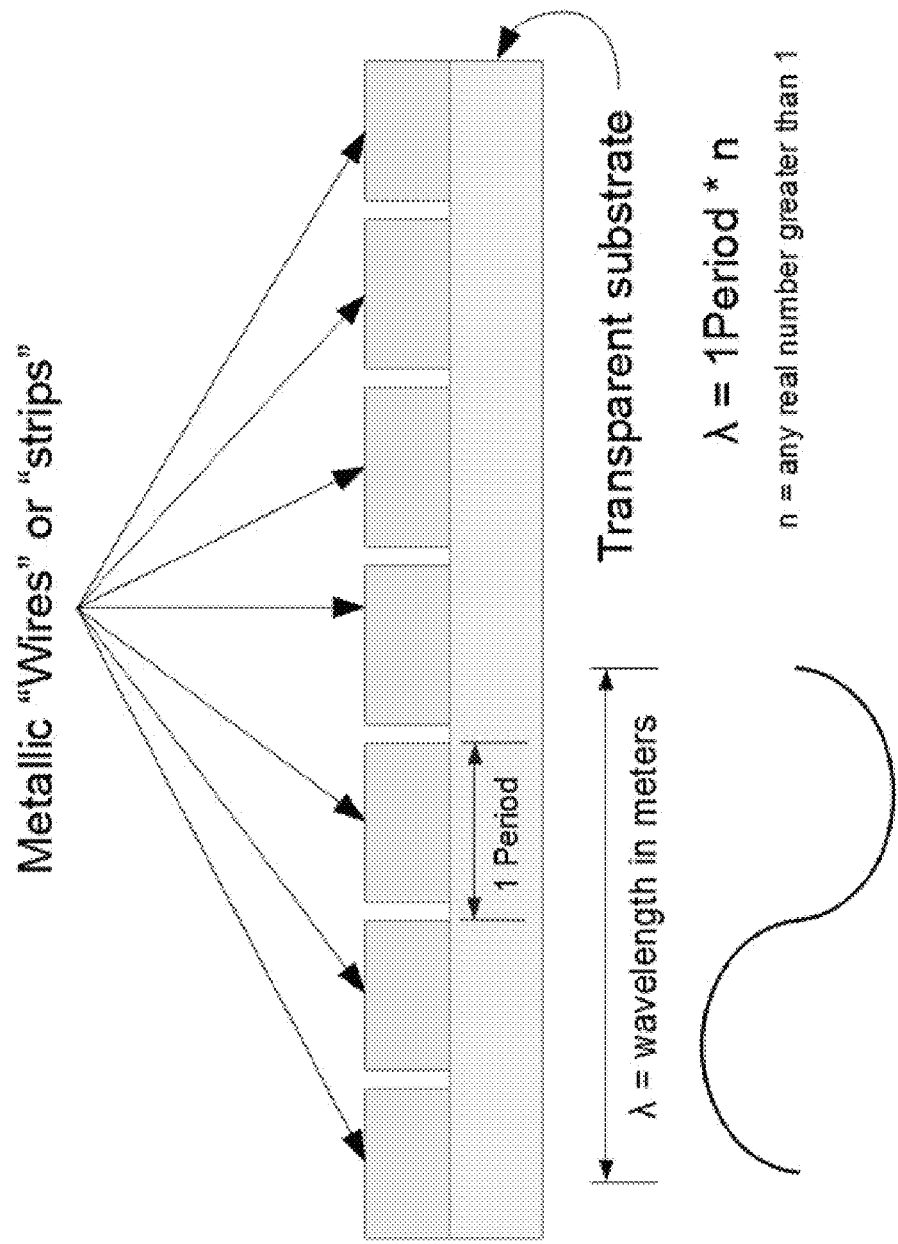
FIG. 6 illustrates a second structured-surface-plasmonic engineering technique, increasing the metal-to-gap ratio in the polarizer to very high fill factors.

The extinction ratio can be increased with careful surface-current engineering that takes advantage of combining two structured-surface-plasmonic engineering techniques. FIG. 5 illustrates the first technique, decreasing the polarizer period to sub-wavelength dimensions, and FIG. 6 illustrates the second technique, increasing the metal-to-free space ratio in the polarizer to very high fill factors (e.g., greater than 90%). In both situations, the wavelength can be a multiple of the polarizer period.

Figure 7:
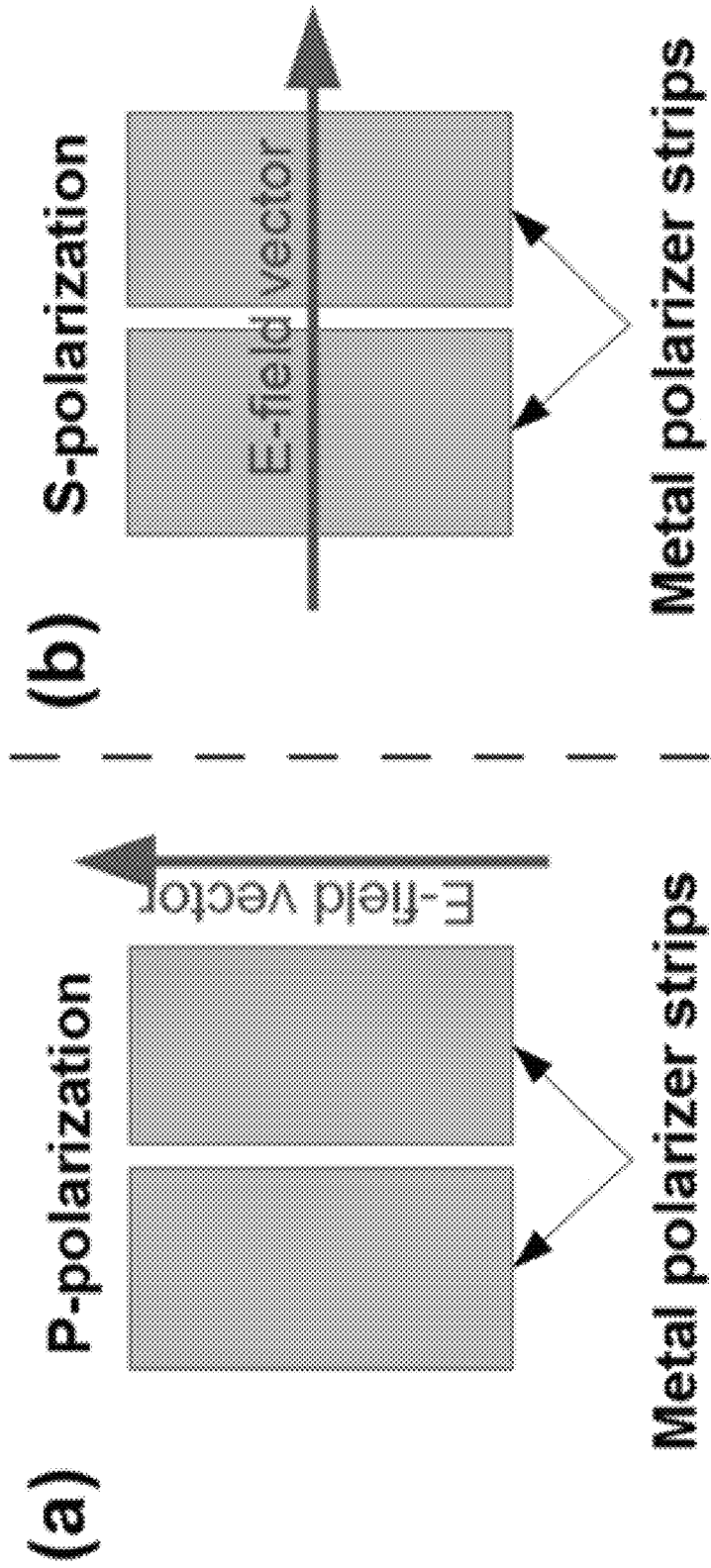
FIG. 7 illustrates a wire-grid polarizer transmitting light for an S-polarized incident wave and blocking light for a P-polarized incident wave, where S- and P-polarization are perpendicular and parallel to the gap, respectively.

For linearly polarized radiation at normal incidence, the amount of transmission through a 1D periodic structure is dependent upon the polarization of the incident radiation. This is because a 1D structure is symmetric in only one dimension. When the electric field vector is parallel to the direction of the wires, it is said to be P-polarized, and is also known as a transverse-magnetic (TM) wave. When the electric field vector is perpendicular to the direction of the wires, it is said to be S-polarized (short for senkrecht, German for perpendicular) and also called a transverse electric (TE) field. In a 1D-periodic structure such as a wire-grid polarizer, P-polarized radiation will be highly attenuated while S-polarized radiation will be mostly transmitted. This is shown graphically in FIG. 7, which illustrates a wire-grid polarizer transmitting light for an S-polarized incident wave and blocking light for a P-polarized incident wave. This behavior is due to the orientation of the currents generated by the incident wave on the surface of the wire conductors. For P-polarized incident waves, the parallel electric field vector will generate surface currents parallel to the wires. Due to fringing effects only small currents will flow into the sides of the wires facing the gaps. These surface currents will oscillate and radiate fields that tend to cancel any transmission through the wire-grid polarizer. For S-polarized incident waves, the perpendicular electric field vector will generate surface currents that flow across and around the wires. These surface currents will radiate in the gaps creating EM dipoles within the gaps as discussed above. These dipoles are coupled to the incoming EM waves. Thus, the dipoles radiate with a frequency of oscillation equal to that of the incident waves and combine with the incident waves and each other in such a manner as to enhance transmission through the structure. Normally incident radiation polarized at angles that are not exactly parallel or perpendicular (i.e., where the polarization angle θ is not parallel (0 or π radians), and not perpendicular (π/2 or 3π/2 radians) will have both parallel and perpendicular components. The parallel component will be blocked and the perpendicular component transmitted, as shown in FIG. 7. Therefore, the amount of radiation transmitted will be less than that from a purely S-polarized wave but more than from a purely P-polarized wave. A similar effect will be seen for radiation incident at oblique angles to the surface of the structure. In this case, both the perpendicular and parallel field components will be reduced in proportion to the cosine of the angle of incidence.

For 2D-periodic arrays, the transmission through the structure will be independent of the polarization. For a normally incident wave with any polarization angle there will always exist a component of the electric field that is parallel to the orientation of the apertures. For radiation incident at oblique angles to the surface of the structure, transmission will again be reduced in proportion to the cosine of the angle of incidence.

As described above and displayed in FIG. 2 at image 220 and in FIG. 3, 1D-periodic metal grid on a dielectric substrate tends to concentrate the electric field of free-space radiation polarized perpendicular to the grid. This concentration occurs in the gap region between neighboring metal strips, and increases inversely with gap dimension up to fill factors of roughly 99%. This rather surprising result can be utilized in a number of THz components and devices. In various embodiments, such components can include 1D- or 2D-periodic metallic-grid arrays on dielectric substrates that have insignificant electromagnetic loss at THz frequencies. In aspects, devices according to the subject innovation can include 1D- or 2D-periodic metallic-grid arrays on substrates made of semiconductor or other functional material, not just a lossless dielectric.

In aspects, one or more devices according to the subject innovation can facilitate impedance transformation from free space to a dielectric substrate. The enhancement factors shown in FIG. 3 pertain to the electric field energy, the electric field magnitude, and the wave impedance in the gap, where the electric field magnitude, $E_G$, is polarized perpendicular to the metal strips. The corresponding magnetic field in the gap, $H_G$, is also concentrated but to a much lesser degree. Hence, the ratio of the transverse components of $E_G$ and $H_G$ is enhanced compared to the free space value, $E_0/H_0 = \eta_0 = 377\Omega$. And because the ratio $E_G/H_G$ is the gap "wave impedance," $Z_G$, then any two-port device located across the gap region will couple to the incident radiation via a much larger source impedance than $\eta_0$. This can be represented through the equivalent circuit shown in FIG. 9. In various embodiments, any of a variety devices in the gap that have high specific differential impedance, $Z_D$, can be placed in the gap, such as zero-bias Schottky diodes, tunnel junctions, and other two-port rectifying devices.

Figure 8:
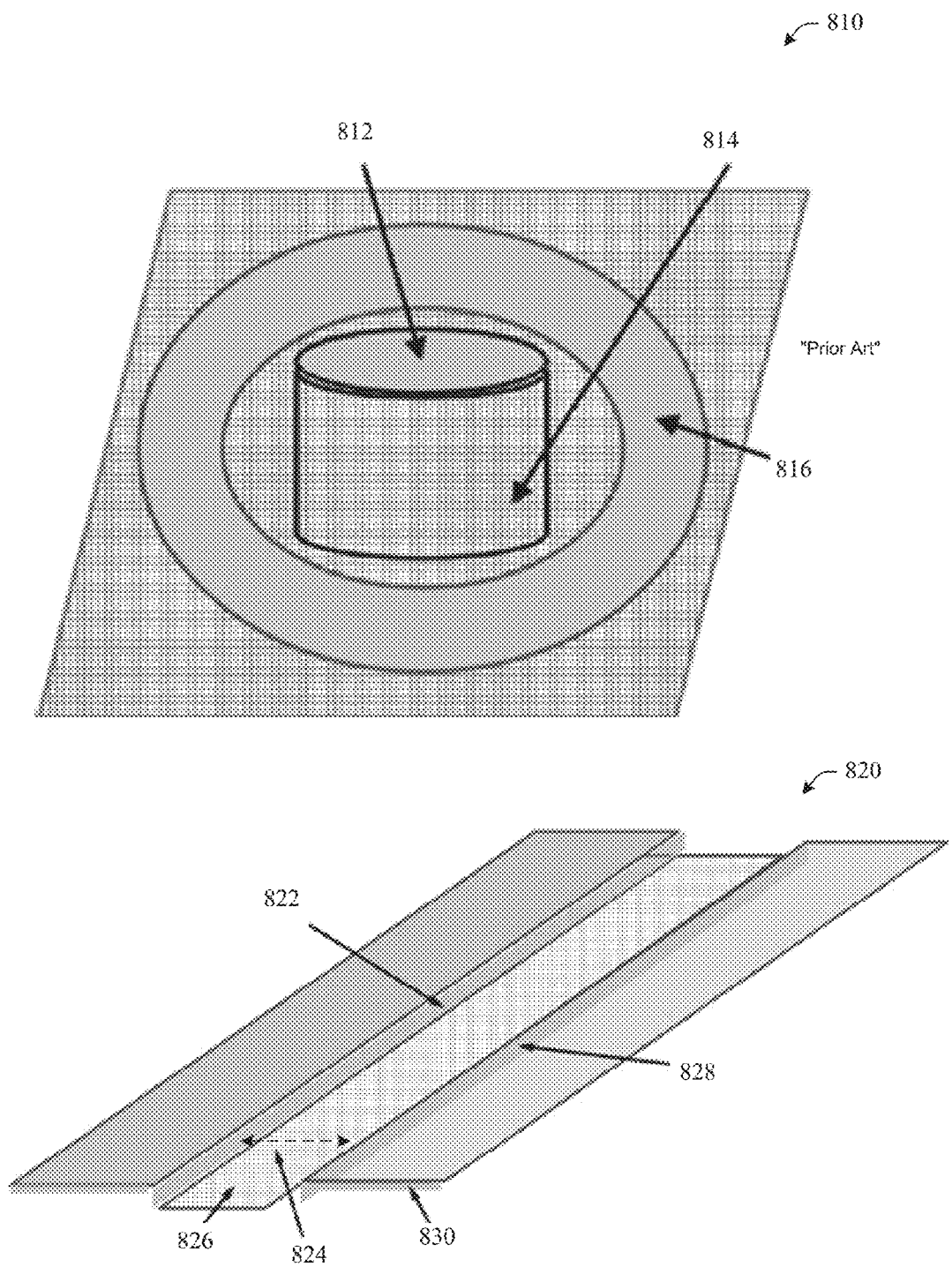
FIG. 8 illustrates a comparison between a conventional mesa-type detector and a distributed detector according to aspects of the subject innovation.

FIG. 8 illustrates a comparison between a conventional detector 810 and a distributed detector 820 according to embodiments of the subject innovation. Based on the concentration effect of high fill-factor wire-grid structures described above, in various aspects, embodiments of the subject innovation can include novel types of THz detector that can be distributed in space along at least one dimension of the underlying substrate. Typically, detectors in the THz region are designed and fabricated with small area to reduce their capacitance. Often, this leads to the vertical (or "mesa") geometry shown by the conventional detector 810 (e.g., a conventional, vertical THz detector) with a top detector junction 812 on a vertical detector mesa 814 and a bottom ohmic contact 816. By contrast, the distributed detector 820 includes a detector contact 822 located on the sidewall of a "gap" 824 (the area exposed to a substrate 826 between the metal strips) of the wire-grid concentrator. The detector contact 822 can be fabricated on one vertical sidewall, and an ohmic contact 828 can be fabricated on the opposite sidewall. An insulating layer 830 can be included to electrically isolate the metal strips from the substrate 826 except at the gap 824. So the distributed detector 820 is physically long compared to the diameter of the mesa of the conventional detector. The distributed detector 820 is also strongly coupled to the incident radiation along its entire length, because of the electromagnetic concentration effects described above.

Figure 9:
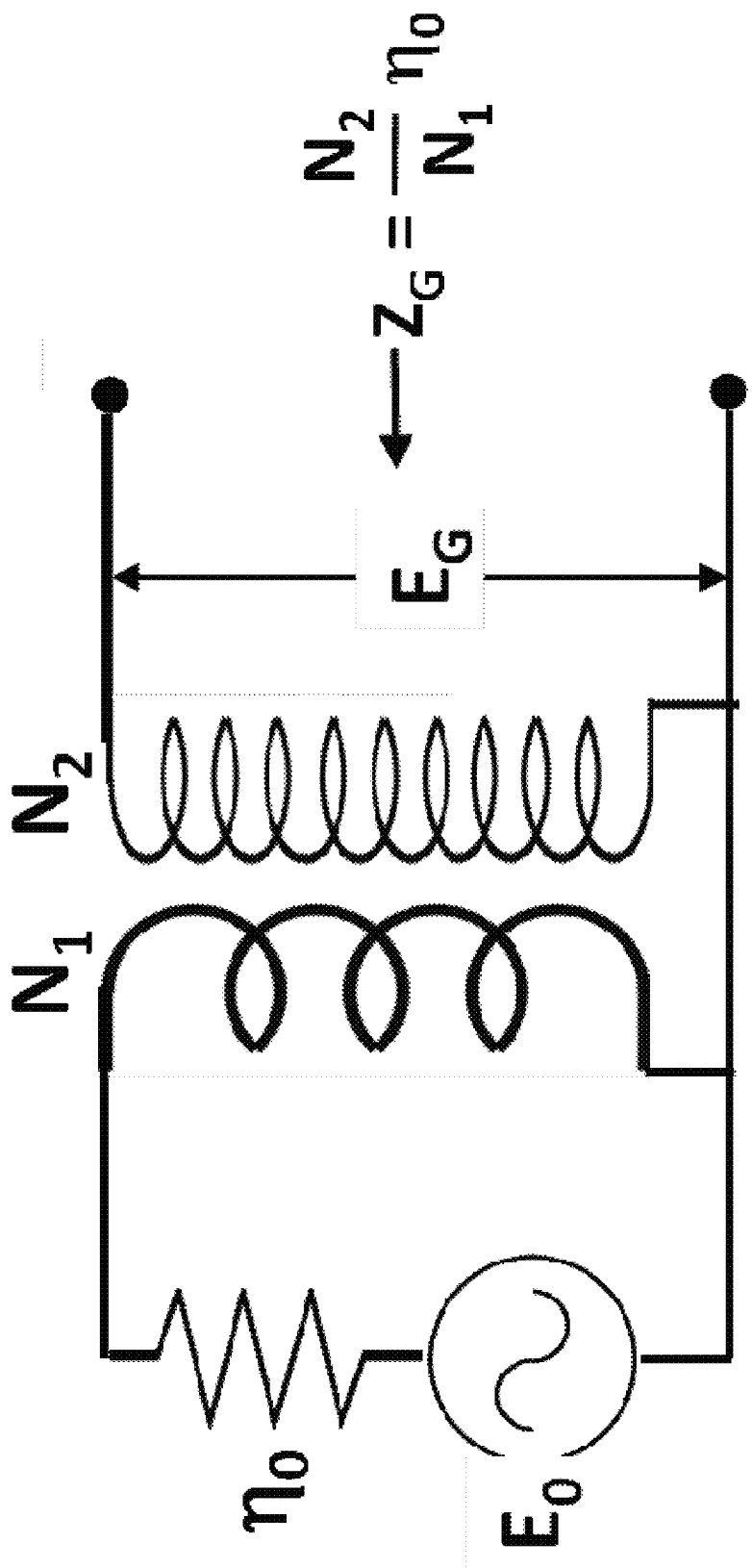
FIG. 9 illustrates the equivalent circuit of a THz wire-grid concentrator.

In the equivalent circuit of FIG. 9, the incident free-space radiation is represented by the ideal generator in series with the impedance $\eta_0$. The role of the wire-grid concentrator is then a "step-up" transformer, boosting the output voltage-to-current ratio. Depending on the type of two-port detector to be located at the output port, they can have a widely variable impedance. For example, the zero-bias Schottky diode represented in FIG. 10 generally has a much higher differential impedance than $\eta_0$. And under this "mismatched" condition, the power "delivered" from free space to the detector should vary as $(|Z_G|/|Z_D|)^2$, so a large increase in power-delivery efficiency can be expected with the step-up transformer compared to coupling directly to the detector from free space. Other types of two-port detectors would also work in this application, for example, unipolar resonant-tunneling diodes (RTDs), bipolar resonant-interband tunnel diodes (RITDs), etc.

Figure 11:
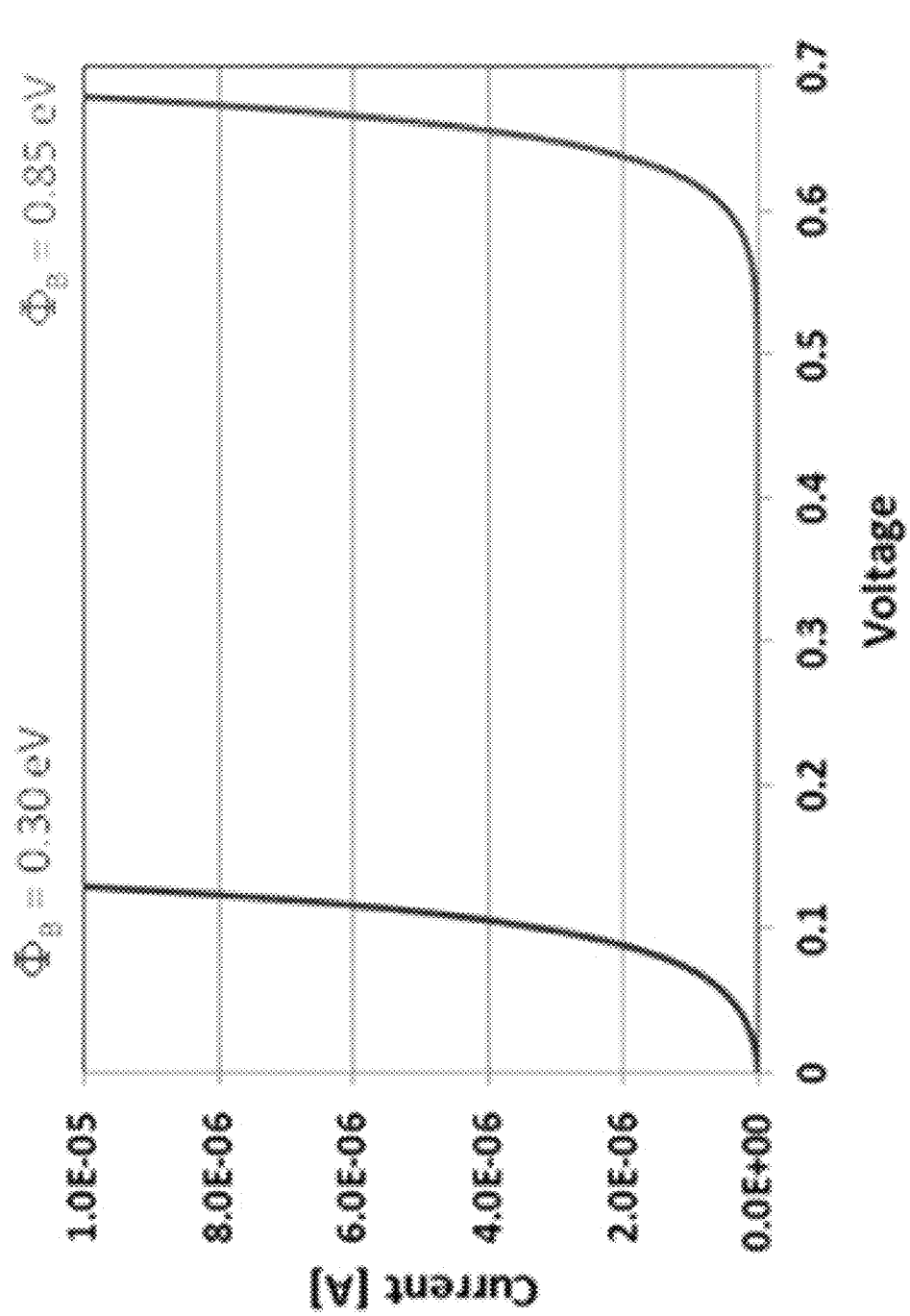
FIG. 11 illustrates the I-V curves of a typical Schottky diode made from a gold-on-GaAs junction and one from a gold-on-InGaAs junction.

One feature of detectors according to aspects of the subject innovation is the ability to display significant rectification properties at zero bias. This can be seen in the current-voltage (I-V) characteristics shown in FIG. 11, which shows the I-V curves of a typical Schottky diode made from two common but different metal-semiconductor junctions of the same: (1) gold-on-GaAs having an electron barrier height $\Phi_B$ of approximately 0.85 eV, and (2) gold-on-InGaAs having an electron barrier height $\Phi_B$ of approximately 0.30 eV. The active area of both devices was 1.0 square micron. The rectifying efficiency, or "responsivity," of such diodes is proportional to the second derivative $d^2I/dV^2$ of the I-V curve, which from elementary calculus is just the "curvature." Hence, by inspection of FIG. 11, the InGaAs Schottky diode has a much higher responsivity at zero bias than the GaAs Schottky diode.

Figure 10:
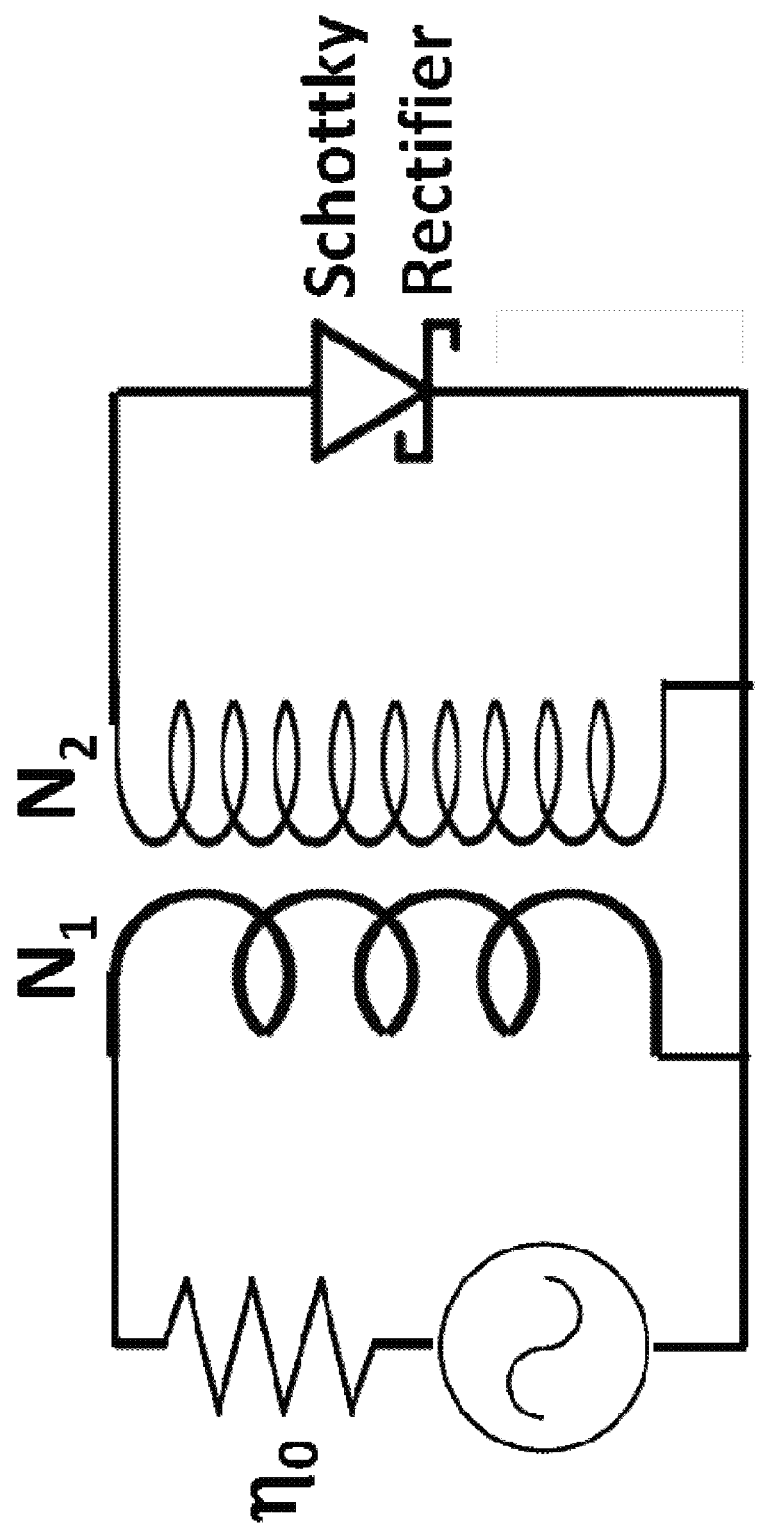
FIG. 10 illustrates the equivalent circuit of a distributed detector based on the concentrator represented in FIG. 9.
Figure 12:
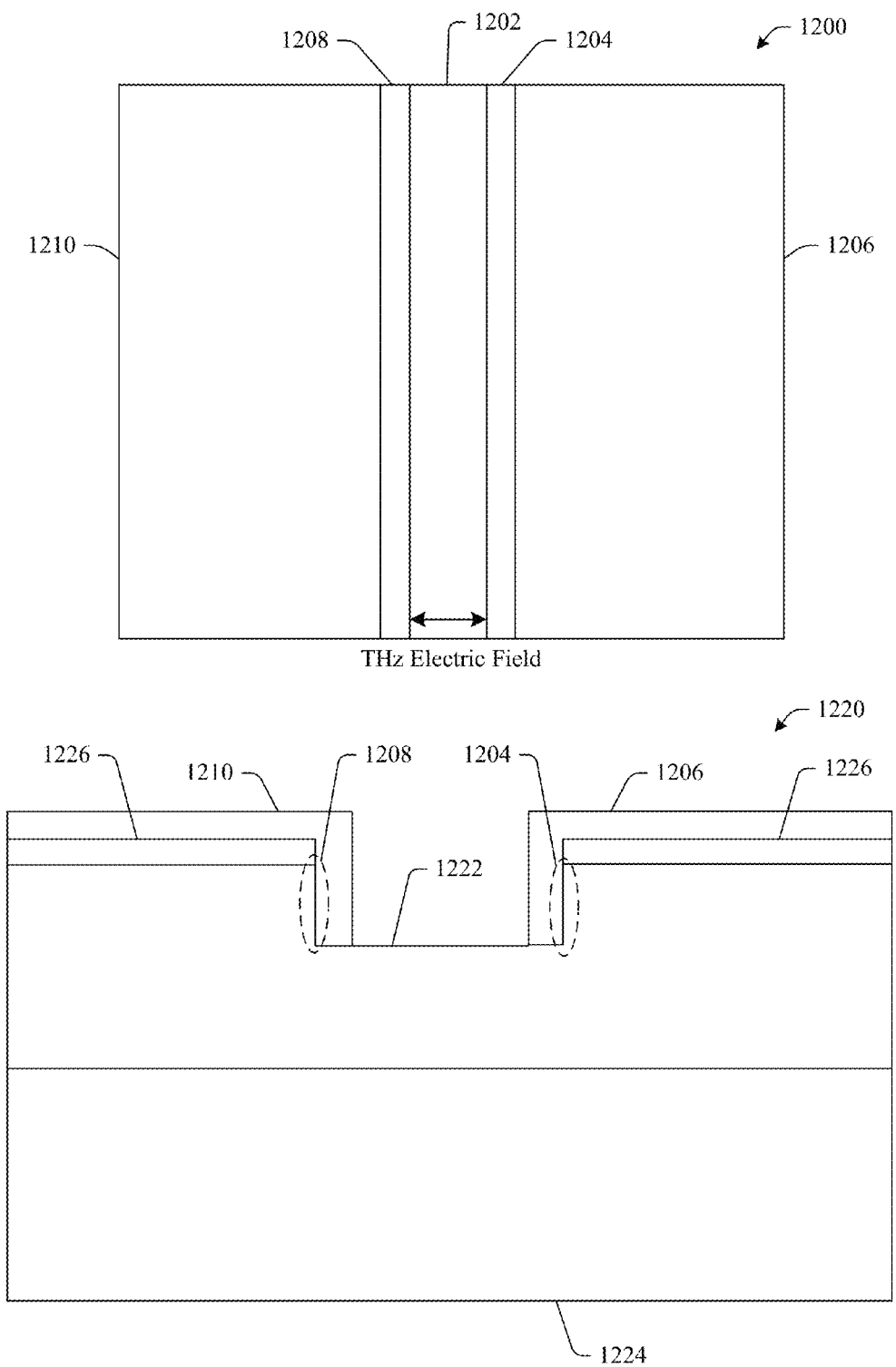
FIG. 12 illustrates a structured-surface-plasmon-engineered, linear distributed THz detector in accordance with aspects of the subject innovation, with the upper image showing the overhead view, and the lower image showing a cross-sectional view.

An important aspect of the transformer coupling to Schottky diodes and other possible detectors in FIG. 10 is that it is inherently a distributed coupling in space. In other words, the ratio $|E|/|H|$ is increased along an entire periphery, not just at one point in space. For the case of wire-grid couplers in FIG. 4, $Z_G = |E_G|/|H_G|$ is increased along the entire length of the slots. Therefore, the tunnel detector, or other THz detector type can also be distributed in space, preferably in such a way that $Z_G$ is constant at all points on the distribution. In accordance with aspects of the subject innovation, one option, as shown in FIG. 12, illustrating a plan view of a 2D-periodic distributed THz detector at 1200, and end view at 1220, is to just distribute the detector uniformly down the gap 1202 where the maximum wave impedance enhancement occurs. Being a two-terminal device, the detector must have two contacts defined, such as a detector junction 1204 (e.g., barrier junction metal contact, etc.) utilizing a detector metal 1206 and an opposite ohmic contact 1208 utilizing ohmic metal 1210 for the Schottky detector embodiments, which are provided as specific examples for the purposes of illustration, although other detectors can be employed in various embodiments.

To see better how the contacts can be made for such a distributed detector, 1220 shows the end view of one possible embodiment, employing a Schottky detector. The semiconductor material can be a doped epitaxial layer 1222, for example, made from a compound semiconductor like GaAs, InGaAs, InAs, InGaSb, or InSb, but also possibly silicon, or germanium. The epitaxial layer 1222 can be deposited on a semi-insulating semiconductor substrate 1224, for example, GaAs, InP, or high-resistivity silicon. The "gap" of the distributed detector can be defined by etching into the epitaxial layer using some form of semiconductor etching, such as wet etching or semiconductor etching. The detector metal-semiconductor contact can then be fabricated on one wall of the gap, and the ohmic metal-semiconductor contact can be fabricated on the opposite wall. Thus, after creation of the gap and contacts, the contacts will extend vertically from the top metal strip layer, past any insulating layer(s), along at least a portion of the doped epitaxial semiconductor layer 1222, to make contact directly with epitaxial layer 1222. In various aspects, gaps of the subject innovation can have widths ranging from around 1 micron to around 10 microns, and can have depths ranging from around 0.1 micrond to around 1.0 micron.

One possible combination would be an n-type $In_{0.53}Ga_{0.47}As$ epitaxial layer on a semi-insulating InP substrate. Except near the edges of the gap, the metallization comprising the metal grids can be isolated from the epitaxial layer by an insulating film 1226, such as silicon oxide or nitride. At one edge the Schottky junction 1204 can be fabricated, and at the opposite edge an ohmic contact 1208 can be fabricated. The difference between obtaining a Schottky or an ohmic depends on the type of metallization. For example, with $In_{0.53}Ga_{0.47}As$, a Schottky junction can be obtained by using pure gold metallization. For the same epitaxial layer, an ohmic can be obtained by using a Ge/Au eutectic alloy and then heating up the sample (above the melting temperature of the alloy) as a last step. It is to be understood that these examples are solely for the purpose of illustrating the concepts of the subject innovation, and numerous other combinations exist for forming ohmic junctions, Schottky junctions, etc.

Figure 13:
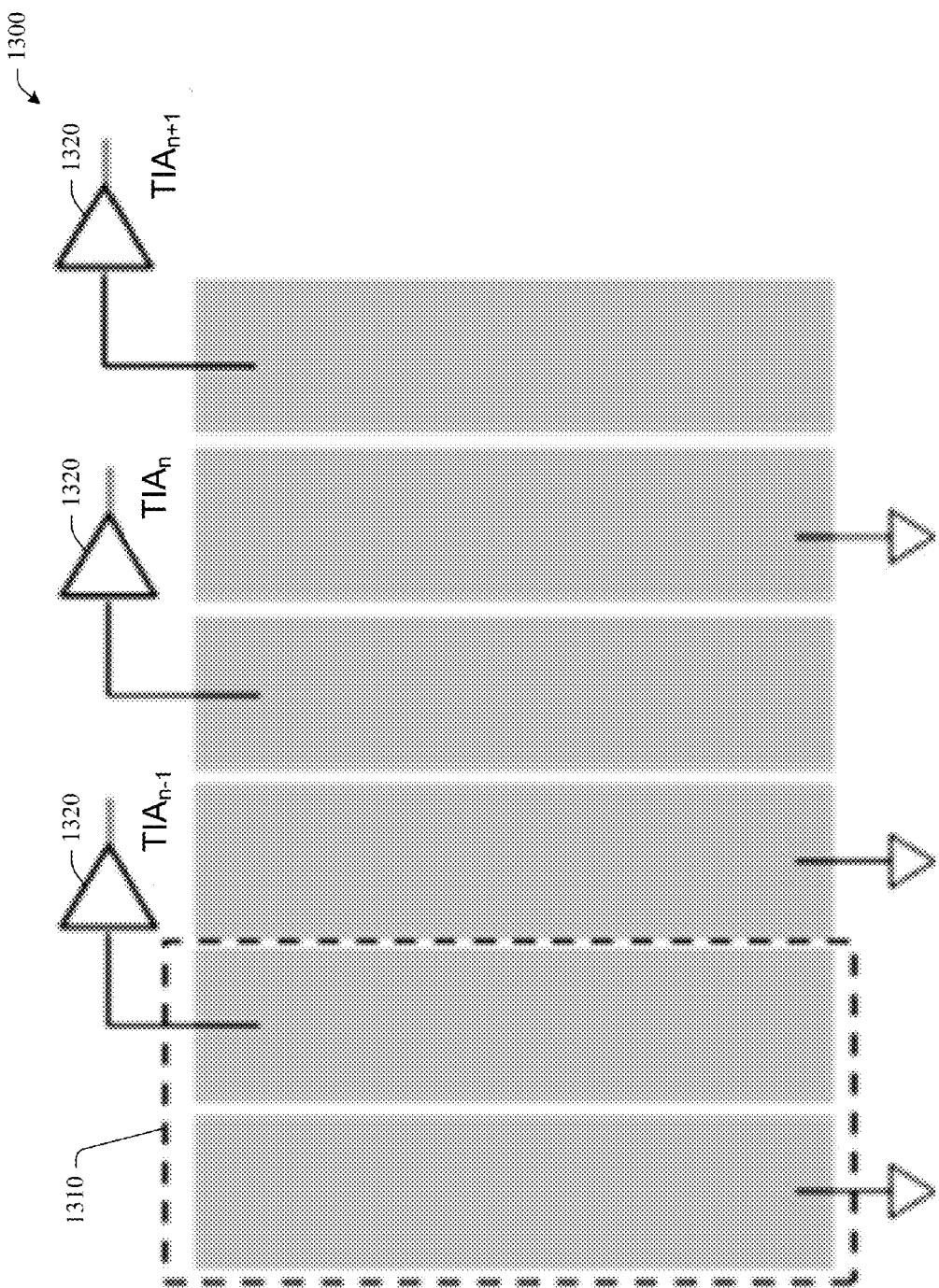
FIG. 13 illustrates a 1D-periodic array of linear distributed detectors as shown in FIG. 12, in accordance with aspects of the subject innovation. The electrical output of each detector is coupled to external circuitry using a transimpedance amplifier (TIA).

Given the layout of FIG. 12, it can be straightforward to read-out the rectified current, such as in the manner shown in FIG. 13, which illustrates a 1D-periodic array 1300 of structured-surface-plasmon-engineered distributed detectors as shown in FIG. 12, with the electrical readout from each unit cell 1310 done with a transimpedance amplifier (TIA) 1320. As shown in FIG. 13, the metal strip on one side of a gap can be grounded, and the metal strip on the opposite side can be connected to a trans-impedance amplifier (TIA) 1320. Modern TIAs can be fabricated with very low noise (voltage and current) so that the noise-equivalent power (NEP) of the detector-TIA combination is not significantly worse than the intrinsic NEP of the detector by itself.

Figure 14:
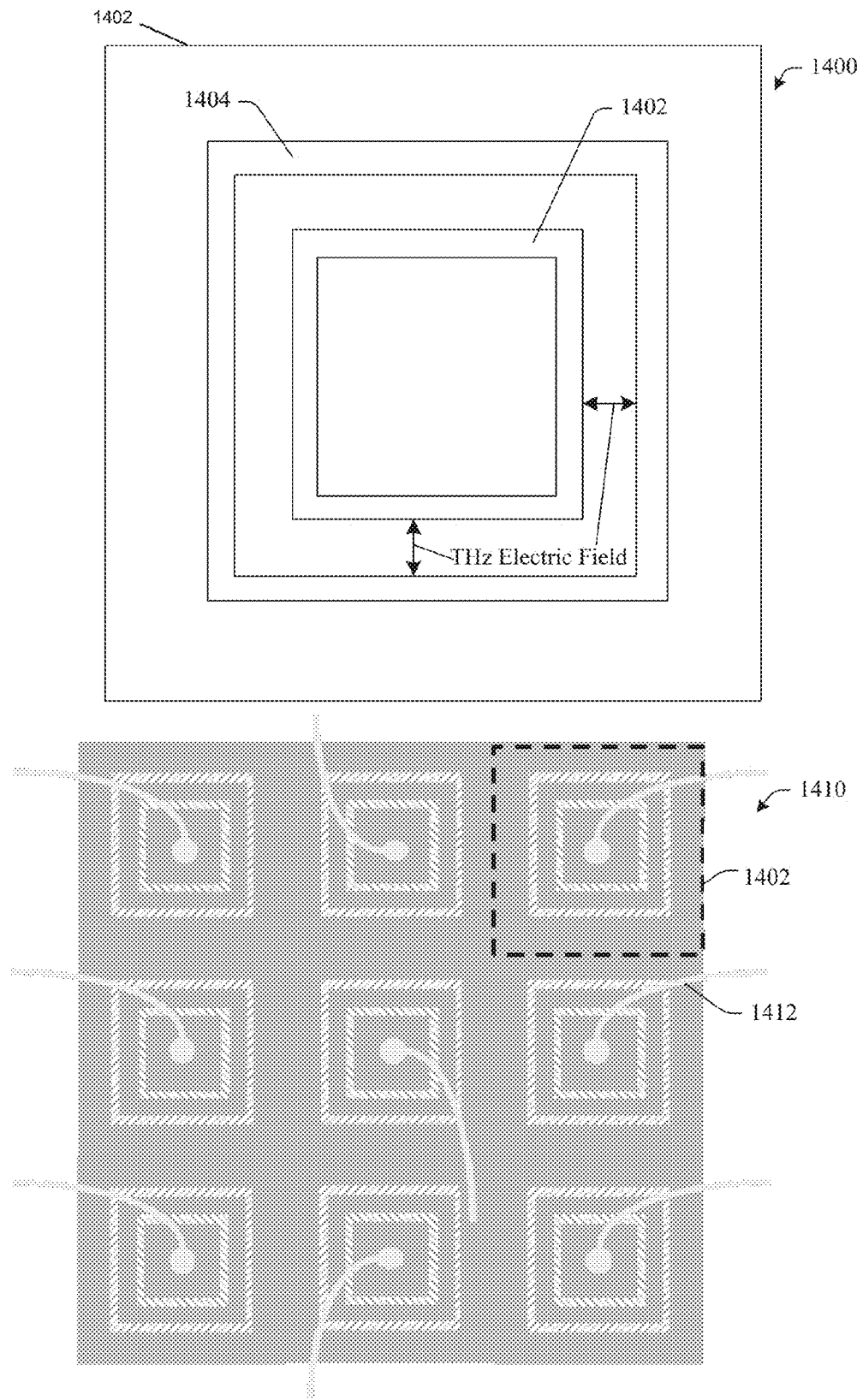
FIG. 14 (upper image) illustrates a top view of a unit cell of a THz distributed detector, and (lower image) a 2D-periodic array of such square distributed detectors, in accordance with aspects of the subject innovation.

In aspects of the subject innovation, the distributed THz detector concept can readily be extended to two dimensions as shown in FIG. 14, illustrating a top view of a unit cell 1406 of a THz distributed detector at 1400 and a 2D array of such square distributed detectors, at 1410. The 2D array includes the unit cell 1406, as indicated by the dashed lines. In this case, the cross-sectional view shown in 1220 applies along two orthogonal axes. In the embodiment shown in FIG. 14, a Schottky or tunnel contact 1402 occurs at the outer rim of an inner square, and an ohmic contact 1404 occurs at the inner rim of an outer square. By repeating the inner square in 2D at the points of a square lattice, a THz detector array such as that shown at 1410 can be obtained. To read out the electronic signal from each detector individually, the inner square of each pixel must be electrically contacted. One example way to do this, as shown at 1410, is by attaching a wire bond 1412 to the top metal contact. An alternative example would be to put metal "bumps" on the top contact and then "bump-bond" to a separate read-out chip. Yet another example would be to contact the inner square by a "via" hole through the substrate, to the bottom side.

Figure 15:
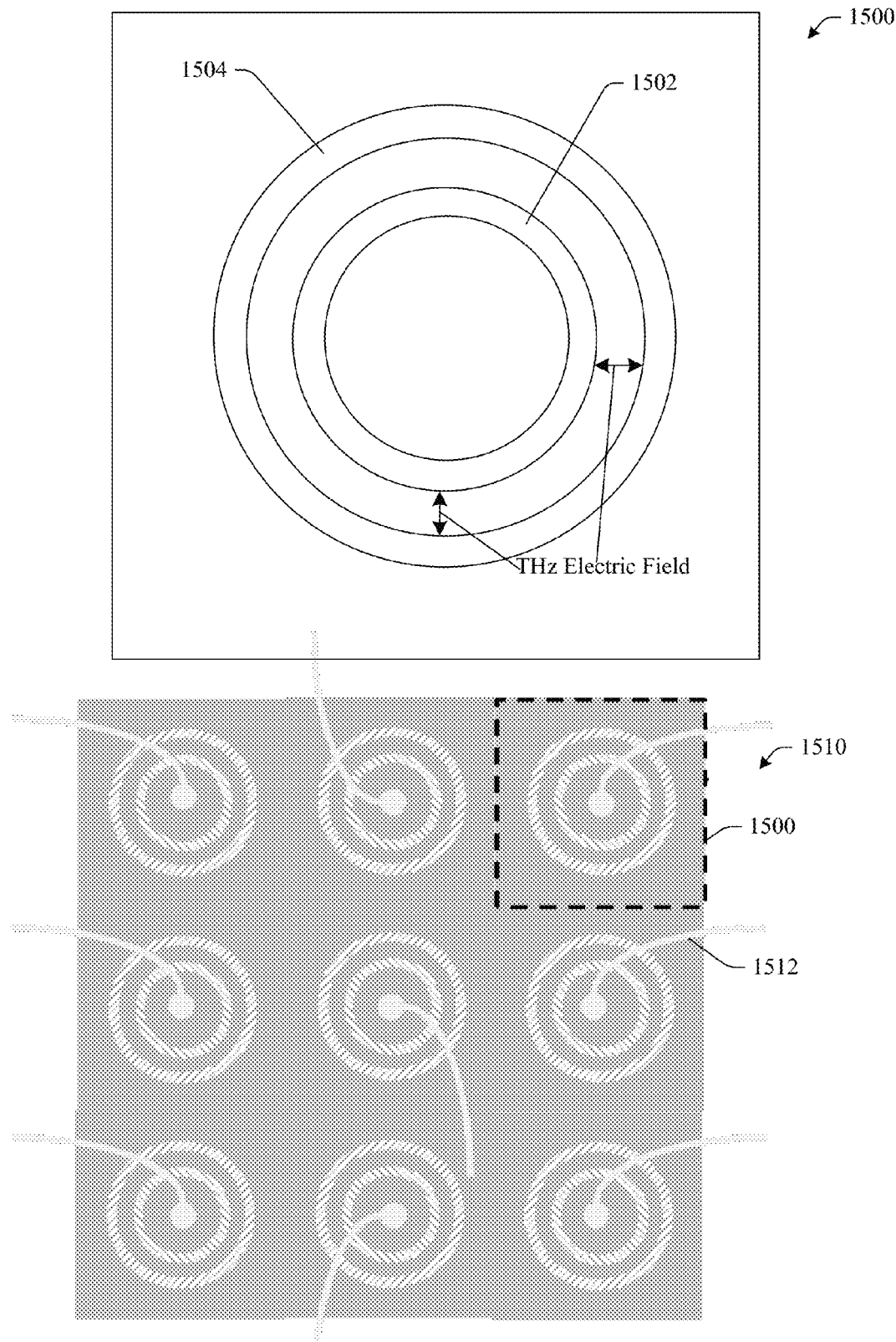
FIG. 15 (upper image) illustrates a unit cell of a circular distributed detector, and (lower image) a 2D-periodic array of such circular distributed detectors, in accordance with aspects of the subject innovation.

FIG. 15 illustrates a similar but alternative detector pixel at 1500 that can be employed in aspects of the subject innovation, showing a top view of a unit cell of a circular distributed detector with detector contact 1502 at the outer rim of an inner circle, and the ohmic contact 1504 at the inner rim of an outer circle. Detector pixel 1500 can also be readily scaled to a 2D array as shown at 1510, and wire bonds 1512 or other electrical connections can be employed. Like the square-pixel approach of FIG. 14, FIG. 15 offers the benefit of uniform response to the polarization of the incident radiation. Although the examples in FIGS. 14 and 15 are provided for purposes of illustration, in various embodiments other designs and geometries can be employed, such as embodiments wherein the gap is any of a variety of closed gaps (e.g., a regular or irregular polygon, ellipse, or other closed plane figure, etc.) enclosing at least one of the detector contact 1502 or the ohmic contact 1504.

In FIG. 14, the square unit cells of the distributed detector array were separated by metal strips. Hence, there was a continuous grid of metal in both dimensions that runs across the array. This was by design, since long metal strips can support large, continuous surface current and create the effect of a ground plane, thereby creating perhaps the largest possible E-field enhancement in the gaps.

Figure 16:
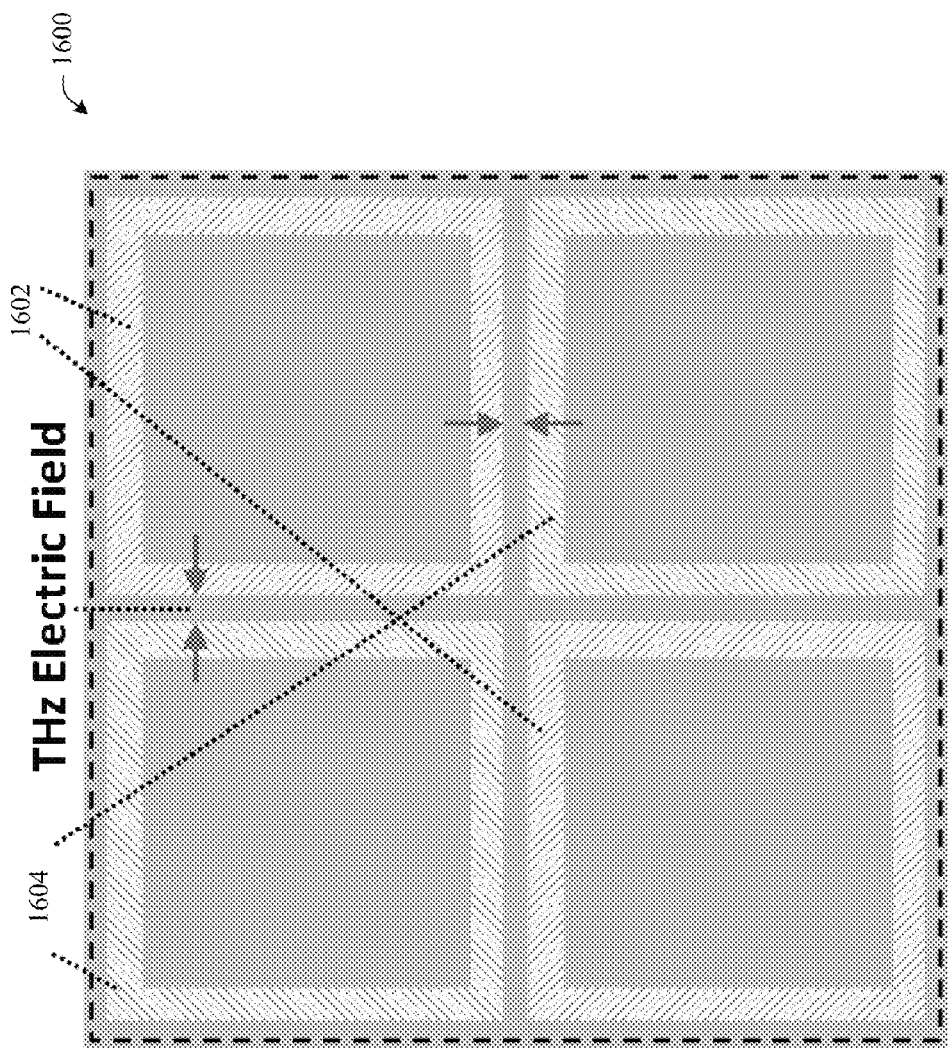
FIG. 16 illustrates a 2D-periodic shared-gap distributed detector design in accordance with aspects of the subject innovation.

FIG. 16 illustrates a shared-gap distributed detector design 1600, another, more compact architecture of a distributed detector array without continuous metal on top. This alternative approach separates detector unit cells by shared gaps. In order to maintain complete detector functionality, the periphery of nearest-neighbor squares must have opposite detector contact types. In other words, if the periphery of a given square is the detector junction 1602, then the periphery of each of its nearest neighbors must be an ohmic contact 1604. Because of the smaller fraction of top metal, design 1600 could ultimately have higher external coupling efficiency. By definition, the coupling efficiency is the fraction of incident power per unit area usefully coupled into the distributed detectors over the same unit area, with "usefully" meaning that the power is converted to detectable, DC current. In various embodiments, other geometries than the square geometry depicted in FIG. 16 could be employed, e.g., an alternating triangular geometry, etc.

Figure 17:
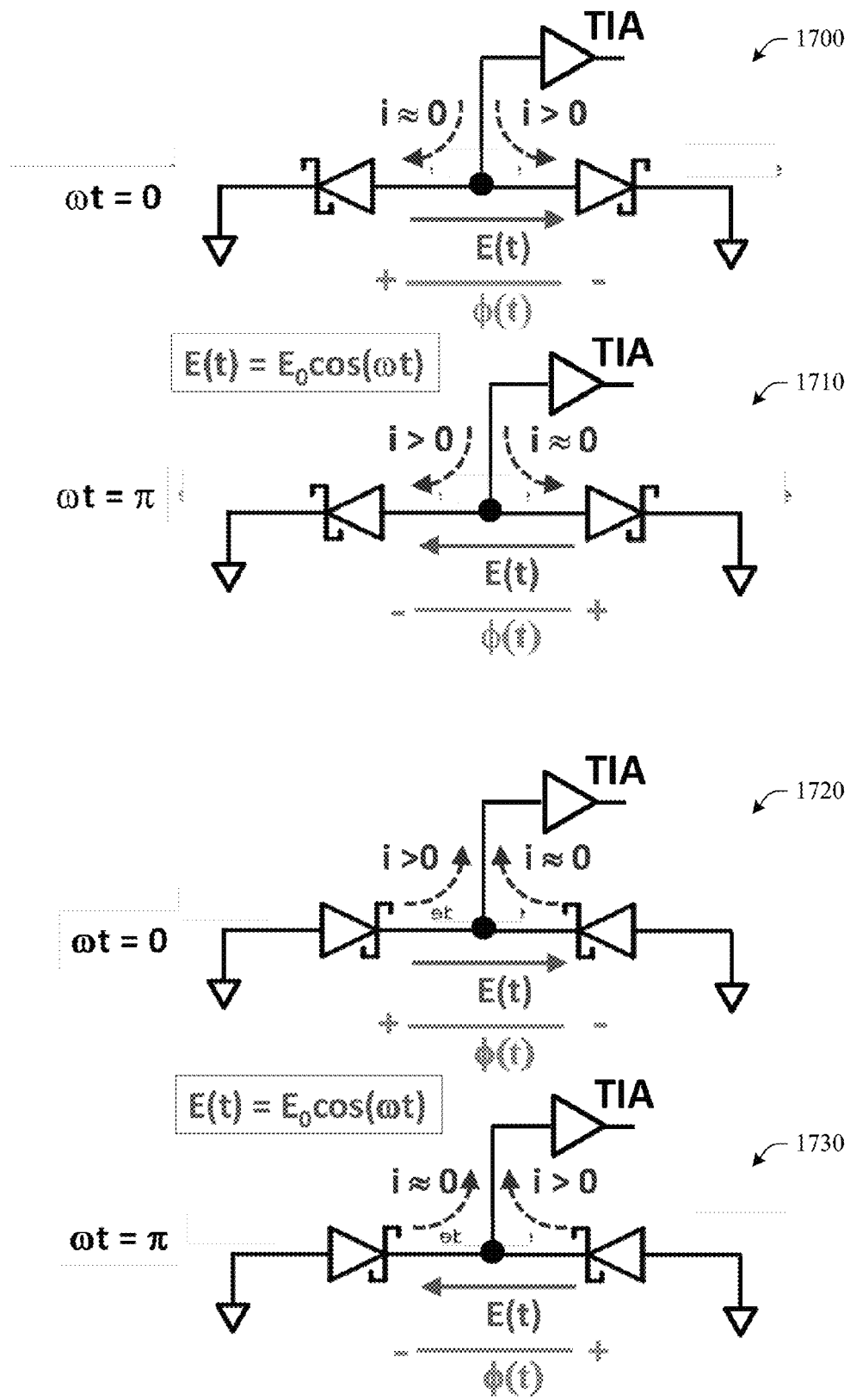
FIG. 17 illustrates the manner in which neighboring distributed detectors combine output currents.

In addition to the distributed detector concept discussed above, there is another aspect that is more subtle, pertaining to the manner in which neighboring detectors in a given unit cell combine their output currents. The simplest way to understand this is shown in FIG. 17, where each of two opposed detectors are represented by the circuit symbols of a Schottky diode aligned in series, but "back-to-back." Assuming that a sinusoidal electric field is incident on the unit cell with a wavelength much longer than the unit-cell width, the instantaneous electric-field can be assumed to be uniform $E=E_0 \cos(\omega t)$, and therefore the instantaneous electrostatic potential $\omega(t)$ can be assumed to be linearly varying from one end of the unit cell to the other.

1700 shows a "snap-shot" of the electric field at t=0, electrostatic potential, and more importantly, the rectified current component i(t) created almost entirely by the detector diode on the right side. 1710 shows a similar "snap-shot" of the electric field 180° later in the cycle at $\omega t = \pi$. At this point in time, the left-side detector diode conducts the current component i(t), and most importantly, in the same direction of i(t) as at $\omega t = 0$. Therefore, over time these two components create a non-zero average, which is easily read-out using the TIA amplifier connected to the common top contact. In essence, the two back-to-back distributed detectors are "cooperative". This same explanation can be generalized to apply to detectors "back-to-back" but oriented in the opposite sense as in 1720 and 1730.

Figure 18:
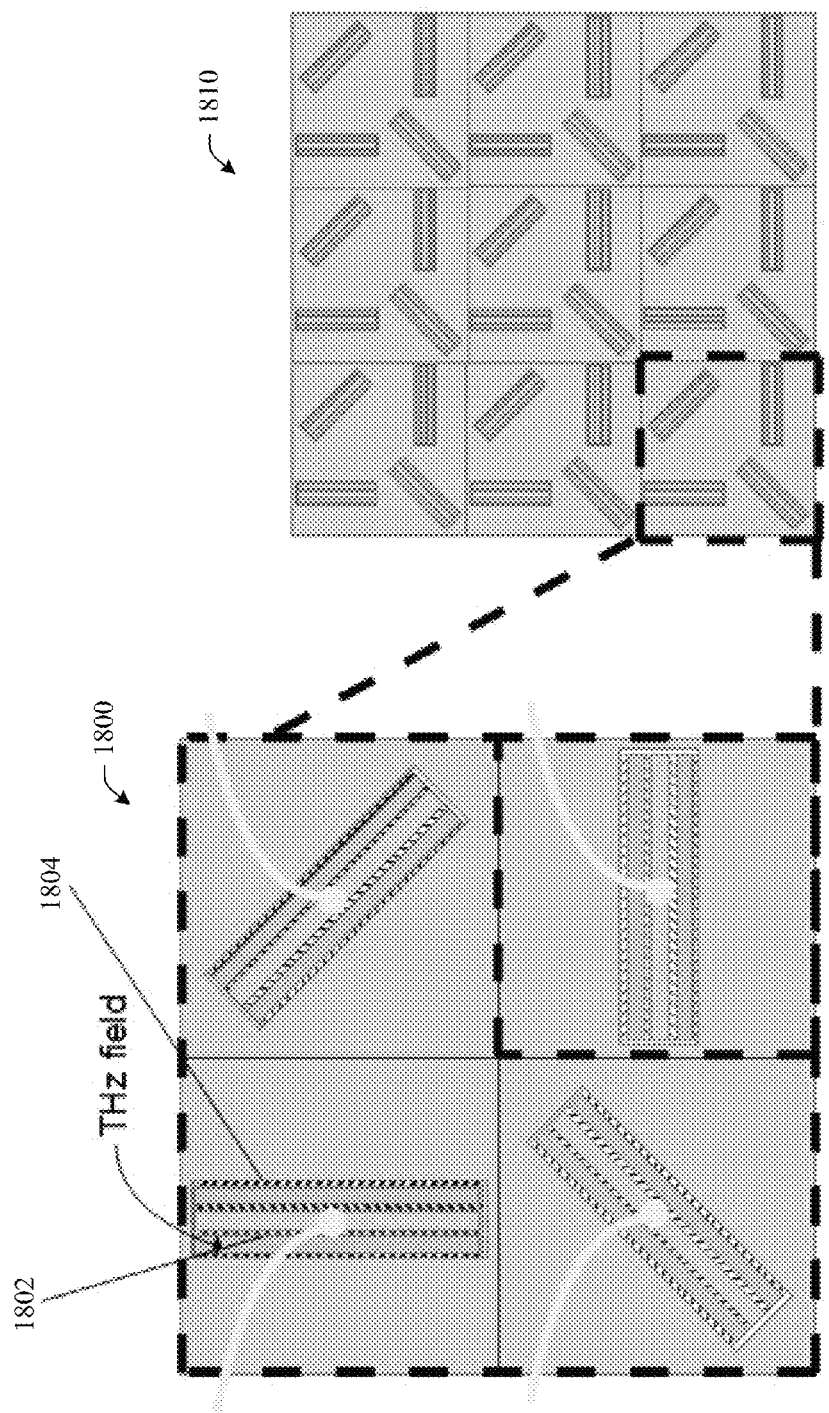
FIG. 18 illustrates a unit cell (left image) and associated 2D-periodic array (right image) for a distributed, polarimetric, THz detector "superpixel" comprising four separate Schottky or tunnel-junction detectors, with each detector sensitive to a different orientation of linear polarization for the incoming radiation, in accordance with various aspects of the subject innovation.

FIG. 18 illustrates another variation on the 2D-periodic detector array, showing a top view of a unit cell for a distributed, polarimetric, THz detector "superpixel" at 1800 that can comprise four separate detectors (and associated array at 1810), with each detector sensitive to different linear polarizations of incoming radiation. It is similar in design to the pixels shown in FIGS. 14 and 15, but the detector junctions 1802 and ohmic contacts 1804 can be only on the long sides of the center contact and surrounding ground plane. The ends of the center contact (or short side) do not contact the ground plane, as a small gap can be maintained there to provide electrical isolation. 1810 shows the structured surface-plasmon enhanced polarimetric superpixel in an array. An array like this can be used to create enhanced imaging techniques, as well as create traditional images similar to what can be done with the technology in FIGS. 14 and 15. The polarization-enhanced techniques available with this array can improve target detection capabilities through clutter suppression. This can be used with active and passive illumination, and with both coherent and incoherent detection.

Figure 19:
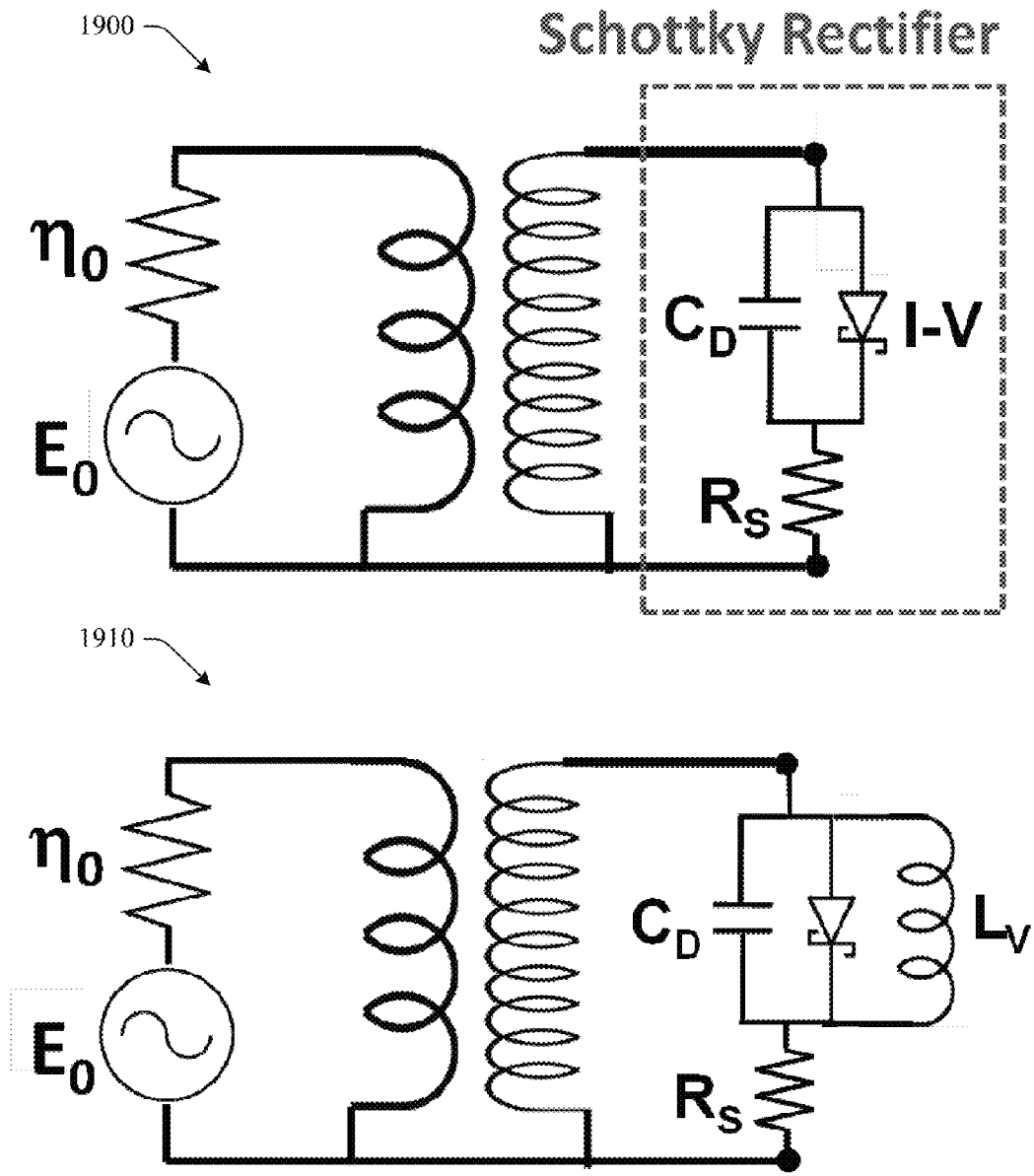
FIG. 19 illustrates equivalent circuits for distributed detectors of the subject innovation, more accurate than those in FIGS. 9 and 10 because of the inclusion of detector (upper image) and embedded-circuit (lower image) reactive effects: a shunt capacitance ($C_D$) for the detector and a shunt inductance ($L_V$) for the circuit.

Unfortunately, in Schottky or tunnel diodes coupled to traditional THz circuits, the I-V curve is not the only story for describing the coupling efficiency and responsivity. Another factor is capacitance, which all solid-state diodes have to some degree. And because of the high dielectric constant of all semiconductors, the specific capacitance (i.e., capacitance per unit area) of Schottky and other detector types is quite high, making the impedance of such devices highly reactive at THz frequencies. A more accurate equivalent circuit of Schottkys and similar detector types at THz frequencies is shown in circuit 1900 of FIG. 19, which illustrates equivalent circuits 1900 and 1910 for distributed detectors of the subject innovation. In 1900, in addition to the device capacitance which appears in shunt with the "resistive" I-V specification, there is also a series resistance $R_S$ which depends on the semiconductor material properties and the details of the fabrication procedure. But it is usually $C_D$ which causes a rapid decay of the THz responsivity with frequency, and a concomitant degradation in the detection sensitivity.

Thus another aspect of embodiments of the innovation disclosed herein is to utilize in the wire grid concentrator structure the presence of large areas of top-side metal as shown in the Figures. This is because the fill-factor of all designs will be very large to get very high E-field enhancement in the gaps, as discussed above. It can then be possible to utilize the top side metal to add another reactive component to the equivalent circuit, an inductor in shunt with the "active" part of the detector, as shown in circuit 1910. Then at a chosen frequency $f_0$ in the THz region, the inductor $L_V$ will "resonate" with the capacitor $C_D$, yielding no net reactance. From simple circuit theory, this frequency is given by $f_0 = [2\pi (C_D L_V)^{1/2}]^{-1}$. Or for a known $C_D$ and a desired operational frequency, this can be solved for $L_V = [(2\pi f_0)^2 C_D]^{-1}$.

In any case, the THz responsivity of the distributed detector will acquire a different frequency dependence. Instead of being monotonically decaying, it will demonstrate a resonant, Lorentzian-like peak centered at $f_0$. An important consequence is a "band-limited" spectral response having bandwidth $\Delta f$. Because of losses in $L_V$ (e.g., THz radiative, etc.) and other parasitic effects, the quality factor Q of the circuit in 1910 is not expected to be very high, most likely under 10 and possibly as small as 2. From circuit theory $Q = f_0/\Delta f$, therefore the expected $\Delta f$ will likely fall in the range between 0.1 $f_0$ and 0.5 $f_0$. So for example, the bandwidth of a distributed detector centered at $f_0 = 600$ GHz would lie between 60 GHz and 300 GHz. The former value works well for coherent active detection and imaging, and the latter value works well for incoherent passive detection and imaging.

Figure 20:
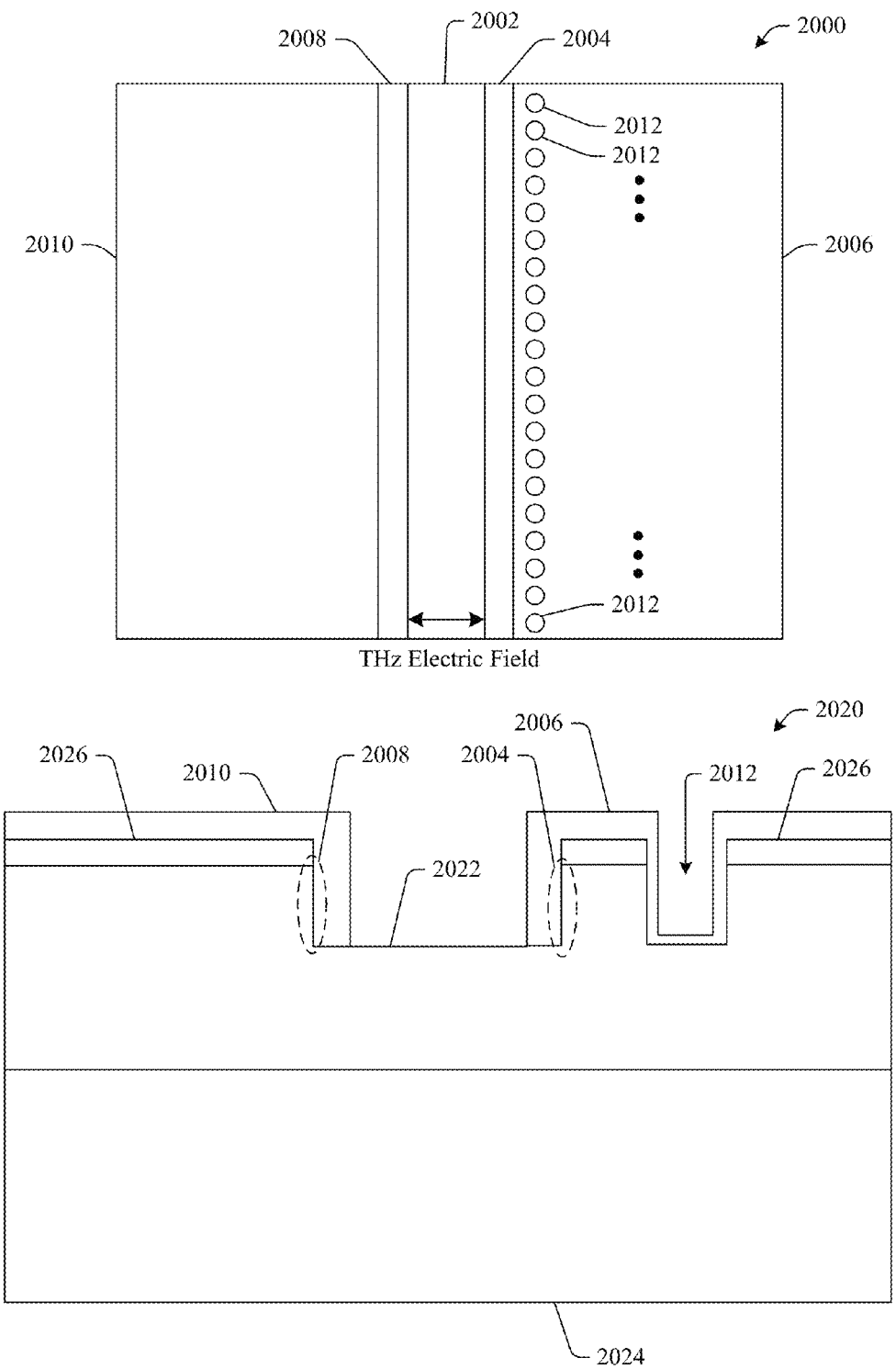
FIG. 20 illustrates one method for realizing the shunt inductance of FIG. 19 for the linear distributed detector of FIG. 12 by inclusion of "via holes" in accordance with aspects of the subject innovation, with the upper image showing the overhead view, and the lower image shows the cross-sectional view.

FIG. 20 illustrates one possible way to create the shunt inductance in a 1D-periodic distributed detector shown in a plan view at 2000 and a side view at 2020. Equivalent elements and features to those in FIG. 12 are numbered similarly. Illustrated are a detector contact 2004, a semi-insulating semiconductor substrate 2024, and an insulating film 2026, similar to FIG. 12. The 1D-periodic distributed detector shown at 2000 also can include a series of "via holes" 2012 in close proximity to the detector junction. As shown in the cross-sectional view, each via hole 2012 can be a cylindrical opening in the active semiconductor layer that can connect detector metal 2006 from the top side (e.g., metal strip, etc.) to a semiconductor 2022 below, roughly at the same vertical level as the bottom of the gap 2002. All inner surfaces of the via hole 2012 can be the same "ohmic metal" 2010 as used to make the ohmic contact 2008 on the left side of 2000. "Via holes" have been used in monolithic microwave and millimeter-wave integrated circuits (i.e., MMICs), especially for bringing two metal layers at different vertical levels in the circuit, into a condition of isopotential. Furthermore, if the via hole 2012 size is small enough, or the frequency is low enough, or both, the primary reactive effect of the via hole 2012 is an inductance, justifying the subscript "V" on the inductor in FIG. 19.

Figure 21:
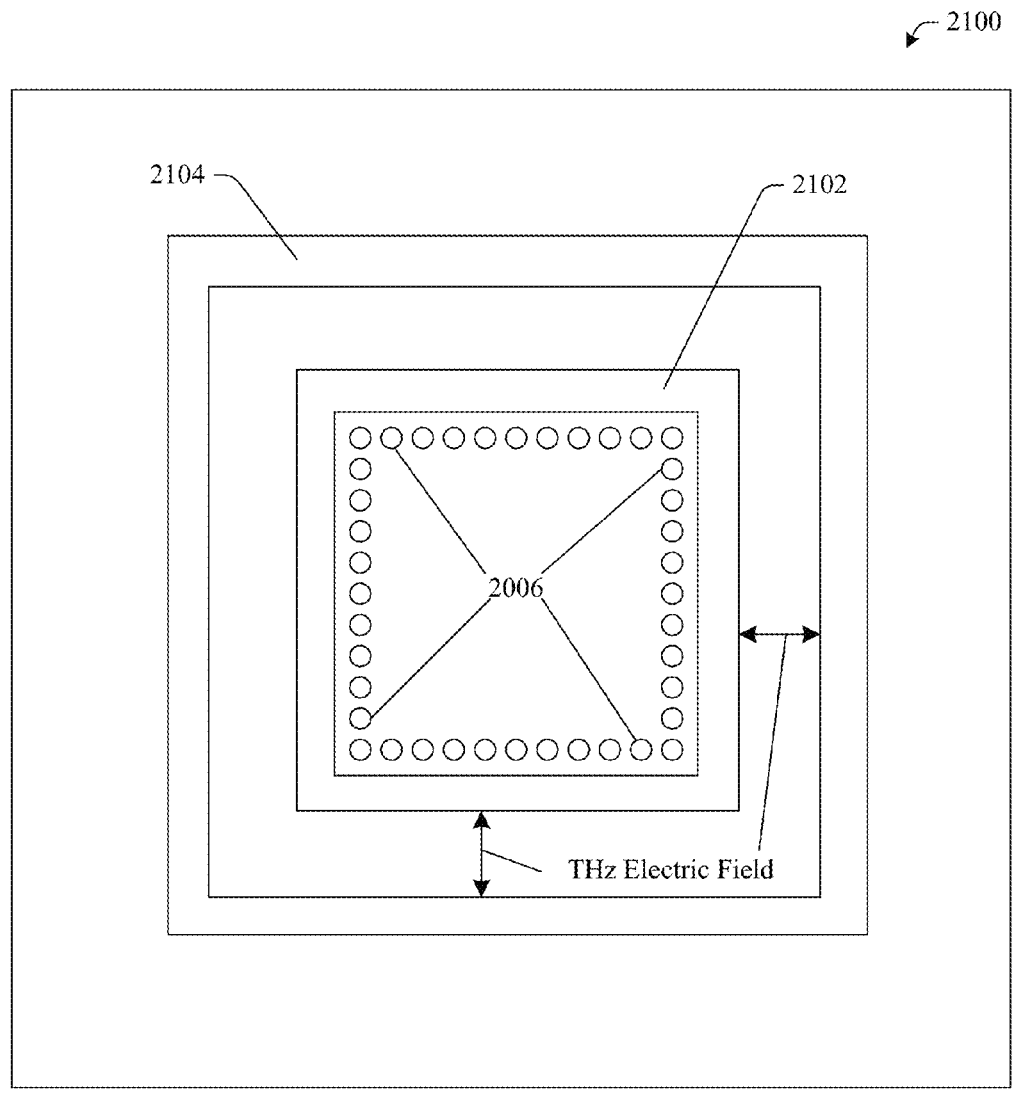
FIG. 21 illustrates the 2D-periodic distributed detector array of FIG. 14 with "via holes" to create the shunt inductance in accordance with aspects of the subject innovation.

FIG. 21 illustrates that the via hole inductance can be generalized to the 2D-periodic distributed detector array shown in 2100, where like elements and features to those in FIG. 14 are numbered similarly. Illustrated are a Schottky or tunnel contact 2102 and an ohmic contact 2104. Here, a square of via holes 2106 can be fabricated just inside the distributed detector periphery. The size and number of holes can be determined by the desired value of $L_V$ as described above by the operating frequency and $C_D$. The fabrication methodology can be identical to that shown in FIG. 20, and the effect of creating a resonant spectral responsivity with "band-limited" performance can also be the same. Additionally, while for the purposes of illustration a square detector with via holes is illustrated, in various aspects, any of a variety of other detectors in accordance with aspects of the subject innovation can include via holes.

Figure 22:
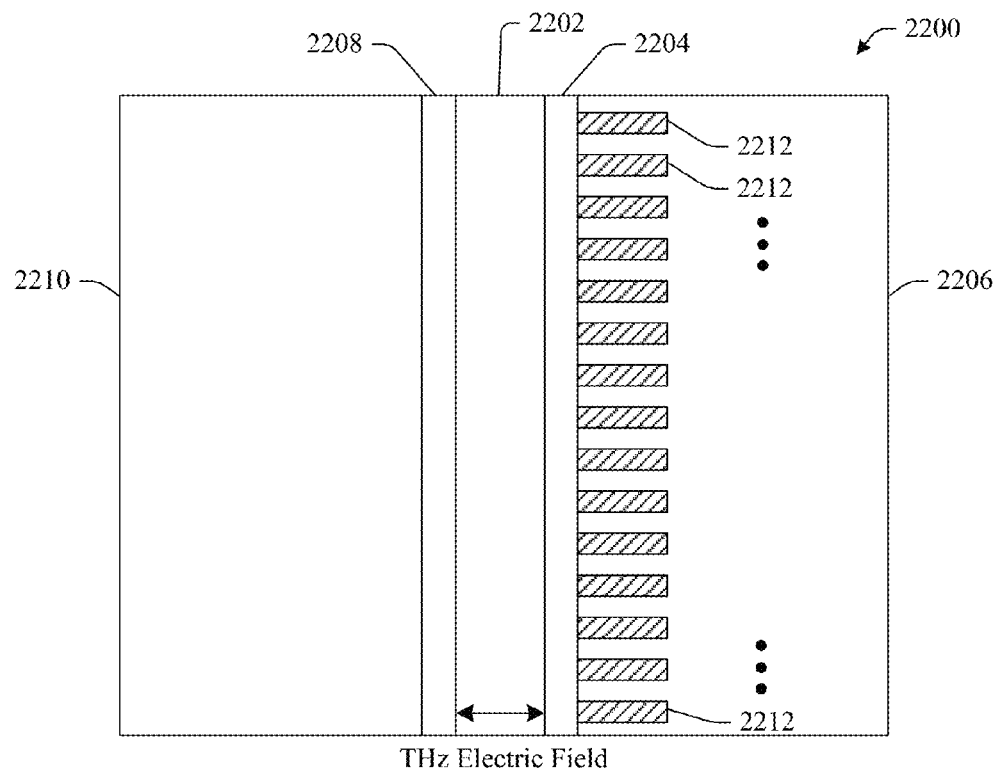
FIG. 22 illustrates a second method for realizing the shunt inductance of FIG. 19 by creating a "leaky wave structure" in accordance with aspects of the subject innovation.
Figure 22:
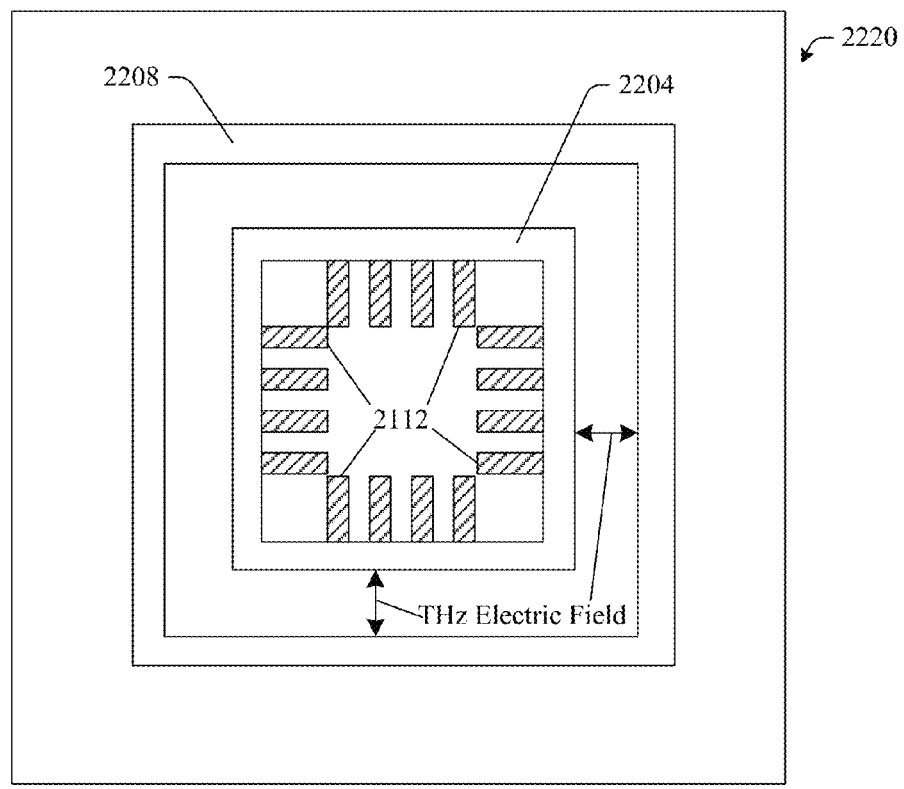

FIG. 22 illustrates, at 2200, another possible way to create distributed shunt inductance in accordance with aspects of the subject innovation. Similar to FIG. 20, FIG. 22 includes a detector junction 2204, a detector metal 2206 utilizing a detector metal 2206 and an opposite ohmic contact 2208 utilizing ohmic metal 2210. An end view is illustrated at 2200. In this case, rectangular grooves 2212 can be fabricated in the top strip adjacent to the gap and to the distributed detector to form a "leaky-wave" structure. The grooves are openings in the top metallic layer that expose the insulator immediately below it (represented by the cross-hatching in FIG. 22). The purpose of these grooves 2212 is to "leak" radiation through the semiconductor "behind" the detector, not on the gap side. Hence the label "leaky wave" structure in FIG. 22. On the semiconductor side, the radiation propagates through a layer of thin oxide and then through a layer of thicker semiconductor having much higher relative dielectric constant $\in_r$ than air (for common semiconductors, $\in_r$ is generally in the range of 12-13). So the "leaked" radiation will propagate downward slower than on the gap side, and therefore add a reactive component to the field (and voltage) across the detector itself. If properly designed, this reactive component can be inductive. Additionally, as with the via holes discussed above, the "leaky wave" structure can be included on any of a variety of detector embodiments in accordance with aspects of the subject innovation.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A distributed surface detector, comprising:
    a detector contact comprising a Schottky or tunnel-junction interface between a semiconductor and a detector metal at a first vertical sidewall of a gap; and
    an ohmic contact comprising an ohmic interface between the semiconductor and an ohmic metal at a second vertical sidewall of the gap, the first vertical sidewall and the second vertical sidewall are located on opposite sides of the gap, the gap defines an area exposed to the semiconductor and separates the detector contact from the ohmic contact, and wherein structured surface plasmons concentrate an electric field in the gap when the distributed surface detector is exposed to THz radiation that is polarized perpendicular to the gap.

2. The distributed surface detector of claim 1, further comprising a transimpedance amplifier that obtains an electrical readout from the distributed surface detector.

3. The distributed surface detector of claim 1, wherein the gap is a closed gap that encloses at least one of the detector contact or the ohmic contact.

4. The distributed surface detector of claim 3, wherein the closed gap is a square gap that encloses the detector contact.

5. A detector array comprising a plurality of unit cells, wherein each unit cell comprises a distributed surface detector according to claim 4.

6. The distributed surface detector of claim 3, wherein the closed gap is a circular gap that encloses the detector contact.

7. A detector array comprising a plurality of unit cells, wherein each unit cell comprises a distributed surface detector according to claim 6.

8. A linear detector array comprising a plurality of unit cells arranged linearly, wherein each unit cell comprises a distributed surface detector according to claim 1.

9. The distributed surface detector of claim 1, wherein the detector metal comprises a plurality of via holes that create a shunt inductance.

10. The distributed surface detector of claim 1, wherein the detector metal comprises a leaky wave structure that creates a shunt inductance.

11. The distributed surface detector of claim 1, wherein a relative width of the gap compared to a width of the detector metal is selected to maximize concentration of the electric field.

12. The distributed surface detector of claim 1, wherein a combined width of the gap and of the detector metal is selected to maximize concentration of the electric field, based at least in part on a wavelength of the THz radiation.

13. A polarimetric distributed surface detector, comprising:
a plurality of unit cells, wherein a unit cell of the plurality of unit cells is aligned to detect a distinct linear polarization, wherein the unit cell comprises:
a detector contact formed at a vertical sidewall of a gap and provides an interface between a semiconductor and a detector metal; and
an ohmic contact formed at another vertical sidewall of the gap, opposite the vertical sidewall, and provides another interface between the semiconductor and an ohmic metal,
the gap exposes a portion of the semiconductor and is located between the detector contact and the ohmic contact, wherein structured surface plasmons concentrate an electric field in the gap when the unit cell is exposed to THz radiation that is polarized perpendicular to the gap.

14. The polarimetric distributed surface detector of claim 13, wherein the plurality of unit cells comprises four unit cells.

15. The polarimetric distributed surface detector of claim 13, wherein at least one unit cell of the plurality of unit cells comprises a strip of detector metal adjacent to the detector contact, and wherein the strip of detector metal comprises a plurality of via holes that create a shunt inductance.

16. The polarimetric distributed surface detector of claim 13, wherein at least one unit cell of the plurality of unit cells comprises a strip of detector metal adjacent to the detector contact, and wherein the strip of detector metal comprises a leaky wave structure that creates a shunt inductance.

17. A detector array comprising a plurality of pixels, wherein each pixel comprises a polarimetric distributed surface detector according to claim 13.

18. A shared-gap distributed surface detector, comprising:
a first detector metal surrounded by a first detector contact formed at a first vertical sidewall of a gap;
a second detector metal surrounded by a second detector contact formed at the first vertical sidewall of the gap;
a first ohmic metal surrounded by a first ohmic contact formed at a second vertical sidewall of the gap; and
a second ohmic metal surrounded by a second ohmic contact formed at the second vertical sidewall of the gap;
the gap defines an area exposed to a semiconductor, the gap separates the first detector contact from the first ohmic contact and from the second ohmic contact, and the gap separates the second detector contact from the first ohmic contact and from the second ohmic contact, wherein structured surface plasmons concentrate an electric field in the gap when the shared-gap distributed surface detector is exposed to THz radiation polarized perpendicular to the gap.

19. The shared-gap distributed surface detector of claim 18, wherein at least one of the first detector metal or the second detector metal comprises a plurality of via holes that create a shunt inductance.

20. The shared-gap distributed surface detector of claim 18, wherein at least one of the first detector metal or the second detector metal comprises a leaky wave structure that creates a shunt inductance.

* * * * *